United States Patent [19]

Pezzuto et al.

[11] Patent Number: 5,962,527
[45] Date of Patent: *Oct. 5, 1999

[54] METHOD AND COMPOSITION FOR TREATING CANCERS

[75] Inventors: John M. Pezzuto; Tapas K. DasGupta, both of River Forest; Mary Lou Schmidt, Chicago; Konrad Marc Kuzmanoff, Berwyn; Lydia Ling-Indeck, Palatine; Darrick S. H. L. Kim, Chicago, all of Ill.

[73] Assignee: The Board of Trustees of the University of Illinois, Urbana, Ill.

[*] Notice: This patent is subject to a terminal disclaimer.

[21] Appl. No.: 08/857,413

[22] Filed: May 16, 1997

Related U.S. Application Data

[63] Continuation-in-part of application No. 08/407,756, Mar. 21, 1995, Pat. No. 5,658,947.

[51] Int. Cl.$^6$ .................................................. A61K 31/20
[52] U.S. Cl. ............................................ 514/569; 514/570
[58] Field of Search ..................................... 514/569, 570

[56] References Cited

U.S. PATENT DOCUMENTS 5,468,888  11/1995  Bouboutou et al. ....................... 554/58

FOREIGN PATENT DOCUMENTS

| WO 95/04526 | 2/1995 | WIPO | ............................. A61K 31/00 |
| WO 96/29068 | 9/1996 | WIPO | ............................. A61K 31/19 |
| WO 96/39033 | 12/1996 | WIPO | ............................. A01N 37/00 |

OTHER PUBLICATIONS

Batta et al., "Crystalline chemical components of some vegetable drugs," *Phytochemistry*, 12, 214–16 (1973).

Otsuka et al., "Studies on anti–inflammatory agents. V. A new anti–inflammatory constituent of *Pyrancantha crenulata roem.*," *Chem. Pharm. Bull.* (Tokyo), 29(11), (Nov., 1981).

Konoshima et al., "Studies on inhibitors of skin–tumor promotion, I. Inhibitory effects of triterpenes from *Euptelea polyandra* on Epstein–Barr virus activation," *J. Nat. Prod.*, 1167–70 (1987).

Rajaram et al., "Constituents of the roots of *Diospyros chloroxylon Roxb*," *Indian Drugs*, 25, 211–12 (1988).

Patent Abstracts of Japan, vol. 013, No. 399, (Sep. 1989).

Ryu et al., "Antitumor triterpenes from medicinal plants," *Archives of Pharm. Research (Seoul)*, 17(5), 375–377 (1994).

Fujioka et al., "Anti–AIDS agents, 11. Betulinic acid and platanic acid as anti–HIV principles from *Syzigium claviflorum*, and the anti–HIV activity of structurally related triterpenoids," *J. Nat. Prod.*, 57, 243–7 (1994).

"News and features. II," *Faseb Journal*, vol. 9, No. 8, 573 (May 1995).

Pisha et al., "Discovery of betulinic acid as a selective inhibitor of human melanoma that functions by induction of apoptosis," *Nat. Med.*, 1(10), pp. 1046–51, (Oct., 1995).

Yasukawa et al., "Some lupane–type triterpenes inhibit tumor promotion by 12–0–tetradecanoylphorbol–13–acetate in two–stage carcinogenesis in mouse skin," *Phytomedicine*, 309–13 (1995).

Del Carmen et al., "Structural requirements for the anti–inflammatory activity of natural triterpenoids," *Planta Medica*, 61/2, 182–185 (1995).

Kashiwada et al., "Betulinic acid and dihydrobetulinic acid derivatives as potent anti–HIV agents," *J. Med. Chem.*, 39, 1016–17 (1996).

"Natural substances in the treatment of melanoma," *Munchener Medizinische Wochenschrift*, 138/7 (18) (1996).

Nagourney et al., "Preliminary analysis of betulinic acid in human tumor primary cultures (meeting abstract)," *Proc. Annu. Meet. Am. Assoc. Cancer Res.*, 37:A2724 (1996).

Evers et al., "Betulinic acid derivatives: A new class of human immunodeficiency virus type 1 specific inhibitors with a new mode of action," *J. Med. Chem.*, 39, 1056–68 (1996).

Bogenrieder et al., "Analysis of pentacyclic triterpene–mediated antiproliferative effects on malignant melanoma cells (Meeting abstract)," *Proc. Annu. Meet. Am. Assoc. Cancer Res.*, 38:A1458 (1997).

Manez et al., "Effect of selected triterpenoids on chronic dermal inflammation," *European Journal of Pharmacology*, vol. 334, No. 1, 103–105 (Sep., 1997).

Ryo et al, Arch. Pharmacol. Res., 17 (1) pp. 375–377, 1994.

Sheth et al, J. Pharm. Sci. 61(11), 1819, 1972.

"Carcinostatics contg. betulin derivs.—having excellent antioncotic activities with less side effects," *Chemical Abstracts*, 89–204083/28, Dec. 1987.

Maurya et al., "Content of betulin and betulinic acid, anti-tumor agents of *Zizyphus* species," *Fitoterapia*, IX, No. 5, pp. 468–469, 1989.

Abstract No. 2724, International Symposium on Advances in Neuroblastoma Research, Meeting Dates—May 22–25, 1996.

Yasukawa et al., "Sterol and triterpene derivatives from plants inhibit the effects of a tumor promoter, and sitosterol and betulinic acid inhibit tumor formation in mouse skin two–stage carcinogenesis," *Oncology*, 48, pp. 72–76, 1991.

*Primary Examiner*—Jerome D. Goldberg
*Attorney, Agent, or Firm*—Marshall, O'Toole, Gerstein, Murray & Borun

[57] ABSTRACT

A composition and method of preventing or inhibiting tumor growth, and of treating malignant cancers without toxic side effects are disclosed. Betulinic acid or a betulinic acid derivative is the active compound of the composition.

3 Claims, 5 Drawing Sheets

Dose Response Curve of Betulinic Acid

Time Course with 2 μg/ml Betulinic Acid

METHOD AND COMPOSITION FOR TREATING CANCERS

CROSS REFERENCE TO RELATED APPLICATIONS

This is a continuation-in-part application of U.S. patent application Ser. No. 08/407,756, filed on Mar. 21, 1995, now U.S. Pat. No. 5,658,947.

This invention was made with government support under U01 CA52956 awarded by the National Cancer Institute. The government has certain rights in the invention.

FIELD OF THE INVENTION

This invention relates to compositions and methods of inhibiting tumor growth and, more particularly, to treating a malignant tumor using plant-derived compounds and derivatives thereof.

BACKGROUND OF THE INVENTION

Over the past four decades the incidence of melanoma has been increasing at a higher rate than any other type of cancer. It is now theorized that one in 90 American Caucasians will develop malignant melanoma in their lifetime. While an increasing proportion of melanomas are diagnosed sufficiently early to respond to surgical treatment and achieve a greater than 90% ten-year survival rate, it is estimated that nearly 7,000 individuals suffering from metastatic melanoma will die in the United States this year.

For patients with metastatic melanoma not amenable to surgical extirpation, treatment options are limited. 5-(3,3-Dimethyl-1-triazenyl)-1-H-imidazole-4-carboxamide (dacarbazine, DTIC) is the most efficacious single chemotherapeutic agent for melanoma having an overall response rate of 24%. But the duration of response to DTIC is generally quite poor. Combination therapy with other synthetic and recombinant agents, including N,N'-bis(2-chloroethyl)-N-nitrosurea (carmustine, BCNU), cisplatin, tamoxifen, interferon-alpha (INF-α) and interleukin-2 (IL-2), has a higher response rate (e.g., 30–50%) in some trials, but a durable complete response rate is uncommon and toxicity is increased. Sequential chemotherapy has promise, but, clearly, current treatment options for individuals suffering from metastatic melanoma are unsatisfactory.

Various drugs derived from natural products, such as adriamycin (doxorubicin) derivatives, bleomycin, etoposide, and vincristine, and their derivatives, have been tested for efficacy against melanoma either as single agents or in combination therapy. However, similar to the synthetic and recombinant compounds, these compounds exhibit low response rates, transient complete responses, and high toxicities.

Nonetheless, as demonstrated by known and presently-used cancer chemotherapeutic agents, plant-derived natural products are a proven source of effective drugs. Two such useful natural product drugs are paclitaxel (taxol) and camptothecin. Paclitaxel originally derived from the bark of the Pacific yew tree *Taxus brevifolia* Nutt. (Taxaceae), currently is used for the treatment of refractory or residual ovarian cancer. More recently, clinical trials have been performed to investigate the possible role of paclitaxel in the treatment of metastatic melanoma. As a single agent, taxol displays activity comparable to cisplatin and IL-2. Taxol functions by a unique mode of action, and promotes the polymerization of tubulin. Thus, the antitumor response mediated by taxol is due to its antimitotic activity. The second drug of prominence, camptothecin, was isolated from the stem bark of a Chinese tree, *Camptotheca acuminata* Decaisne (Nyssaceae). Camptothecin also functions by a novel mechanism of action, i.e., the inhibition of topoisomerase I. Phase II trials of a water-soluble camptothecin pro-drug analog, Irinotican (CPT-11), have been completed in Japan against a variety of tumors with response rates ranging from 0% (lymphoma) to 50% (small cell lung). Topotecan, another water-soluble camptothecin analog, currently is undergoing Phase II clinical trials in the United States.

Previous antitumor data from various animal models utilizing betulinic acid have been extremely variable and apparently inconsistent. For example, betulinic acid was reported to demonstrate dose-dependent activity against the Walker 256 murine carcinosarcoma tumor system at dose levels of 300 and 500 mg/kg (milligrams per kilogram) body weight. In contrast, a subsequent report indicated the compound was inactive in the Walker 256 (400 mg/kg) and in the L1210 murine lymphocytic leukemia (200 mg/kg) models. Tests conducted at the National Cancer Institute confirmed these negative data.

Similarly, antitumor activity of betulinic acid in the P-388 murine lymphocyte test system has been suggested. However, activity was not supported by tests conducted by the National Cancer Institute. More recently, betulinic acid was shown to block phorbol ester-induced inflammation and epidermal ornithine decarboxylase accumulation in the mouse ear model. Consistent with these observations, the carcinogenic response in the two-stage mouse skin model was inhibited. Thus, some weak indications of antitumor activity by betulinic acid have been reported, but, until the present invention, no previous reports or data suggested that betulinic acid was useful for the selective control or treatment of human melanoma. Furthermore, to date, no information has been published with respect to the selective activity of derivatives of betulinic acid against melanoma cells.

In addition, although betulinic acid has demonstrated a selectivity with respect to inhibiting malignant melanoma, additional studies have shown that betulinic acid, and betulinic acid derivatives, can inhibit other types of cancer cells, such as neuroblastoma.

SUMMARY OF THE INVENTION

The present invention is directed to a method and composition for preventing or inhibiting tumor growth. The active compound is betulinic acid or a derivative of betulinic acid. Betulinic acid can be isolated by a method comprising the steps of preparing an extract from the stem bark of *Ziziphus mauritiana* and isolating the betulinic acid. Alternatively, betulin can be isolated from the extract and used as precursor for betulinic acid, which is prepared from betulin by a series of synthetic steps.

The betulinic acid can be isolated from the extract by mediating a selective cytotoxic profile against human melanoma in a subject panel of human cancer cell lines, conducting a bioassay-directed fractionation based on the profile of biological activity using cultured human melanoma cells (MEL-2) as the monitor, and obtaining betulinic acid therefrom as the active compound. The resulting betulinic acid can be used to prevent or inhibit tumor growth, or can be converted to a derivative to prevent or inhibit tumor growth.

An important aspect of the present invention, therefore, is to provide a method and composition for preventing or inhibiting tumor growth and, particularly, for preventing or inhibiting the growth of a malignant tumor using a natural product-derived compound, or a derivative thereof.

Another aspect of the present invention is to provide a treatment method using betulinic acid, or a derivative thereof, to prevent the growth or spread of cancer cells, wherein betulinic acid, or a derivative thereof, is applied in a manner consistent with treatment of the cancer, e.g., in a topical preparation for the inhibition, prevention, or treatment of a melanoma, or intravenously or intraperitoneally for other forms of cancer.

Another aspect of the present invention is to overcome the problem of high mammalian toxicity associated with synthetic anticancer agents by using a natural product-derived compound, e.g., betulinic acid or a derivative thereof.

Yet another aspect of the present invention is to provide a composition and method of treating forms of cancer, in addition to melanoma, with a naturally occurring product, or a derivative thereof. In particular, the present invention is directed to inhibiting malignant tumor growth associated with neuroblastoma, breast cancer, lung cancer, fibrosarcoma, colon cancer, oral epidermoid carcinoma, epidermoid carcinoma, prostate cancer, hormone-dependent breast cancer, and glioma.

Still another aspect of the present invention is to overcome the problem of insufficient availability associated with synthetic anticancer agents by utilizing readily available, and naturally occurring, betulinic acid, or a derivative thereof.

Yet another aspect of the present invention is to prepare derivatives of betulinic acid that have activity against cancer cells, and that have physical properties that make the derivatives easier to incorporate into compositions that can be administered to an individual for the prevention or inhibition of cancer cell growth.

These and other aspects of the present invention will become apparent from the following description of the invention, which are intended to limit neither the spirit or scope of the invention but are only offered as illustrations of the preferred embodiments of the invention.

DETAILED DESCRIPTION OF THE PREFERRED EMBODIMENTS

Figure 1:
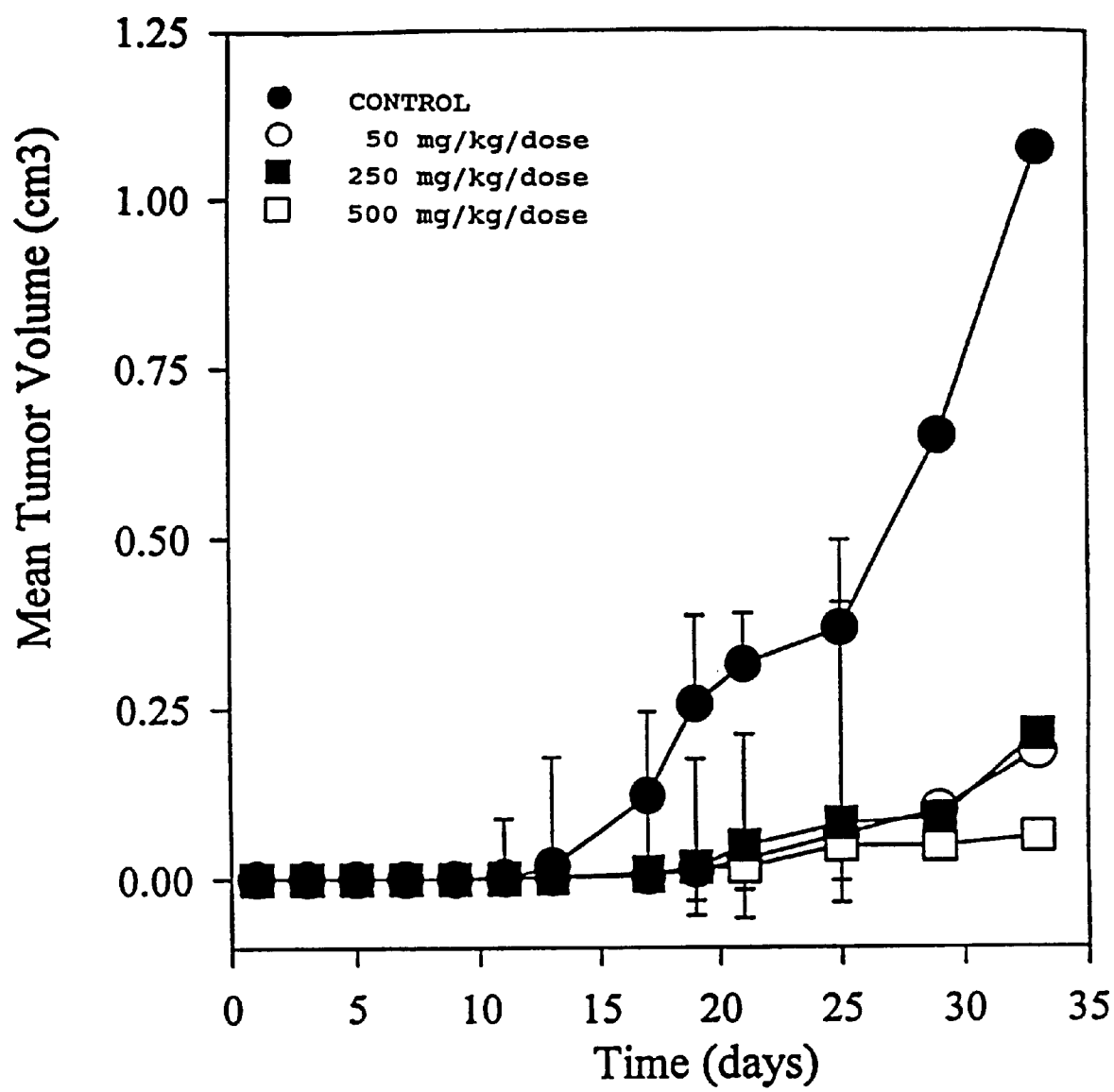
FIG. 1 is a plot of mean tumor volume (in cubic centimeters ($cm^3$)) vs. time for nonestablished MEL-2 tumors in control mice and mice treated with increasing dosages of betulinic acid.

Betulinic acid, 3β-hydroxy-lup-20(29)-ene-28-oic acid, is a natural product isolated from several genus of higher plants. Through a bioassay-directed fractionation of the stem bark of *Ziziphus mauritiana* Lam. (Rhamnaceae), betulinic acid, a pentacyclic triterpene, was isolated as an active compound that showed a selective cytotoxicity against cultured human melanoma cells and against other cancer cell lines. The cell lines evaluated for cytotoxicity were A431 (squamous), BC-1 (breast), COL-2 (colon), HT-1080 (sarcoma), KB (human oral epidermoid carcinoma), ZR-75-1 (hormone-dependent human breast cancer), LNCaP (prostate), LU-1 (lung), U373 (glioma), neuroblastoma, and MEL-1, -2, -3, and -4 (melanoma). Betulinic acid was found to be an excellent antitumor compound against human melanoma due to its unique in vitro and in vivo cytotoxicity profile. Betulinic acid also was found to have activity against the other cancer cell lines that were tested.

In particular, betulinic acid has shown a strong selective antitumor activity against melanoma by induction of apoptosis. The selective cytotoxicity of betulinic acid, and its lack of toxicity toward normal cells, afford a favorable therapeutic index. In addition, betulinic acid has been reported to have an anti-HIV activity.

The bark of white birch, *Betula alba*, contains betulin (up to about 25%), lup-20(29)-ene-3β,28-diol, and betulinic acid (0.025%), but it is difficult to isolate a sufficient quantity of betulinic acid to perform an extensive bioassay. It has been found that a quantity of betulinic acid could be provided from betulin through a synthetic approach. A number of multi-step synthetic conversions of betulin to betulinic acid have been reported, but these synthetic sequences suffer from a low overall yield. A concise two-step conversion of betulin to betulinic acid, in good yield, has been reported in *Synthetic Communications*, 27(9), pp. 1607–1612 (1997).

As shown in Table 1, in vitro growth of MEL-2 cells was inhibited by betulinic acid, i.e., an $ED_{50}$ value of about 2 µg/ml. However, none of the other cancer cell lines tested by this method, i.e., Method A, was affected by betulinic acid (i.e., $ED_{50}$ values of greater than 20 µg/ml). Such clearly defined cell-type specificity demonstrated by betulinic acid is both new and unexpected.

For example, as illustrated in Table 1, other known antitumor agents, such as paclitaxel, camptothecin, ellipticine, homoharringtonine, mithramycin A, podophyllotoxin, vinblastine and vincristine, demonstrated relatively intense, nonselective cytotoxic activity with no discernible cell-type selectivity. Moreover, the cytotoxic response mediated by betulinic acid is not exclusively limited to the MEL-2 melanoma cell line. Dose-response studies performed with additional human melanoma cell lines, designated MEL-1, MEL-3 and MEL-4, demonstrated $ED_{50}$ values of 1.1, 3.3 and 4.8 µg/ml, respectively.

In the following Table 1, the extracted betulinic acid and the other pure compounds were tested for cycotoxity against the following cultured human cell lines: A431 (squamous cells), BC-1 (breast), COL-2 (colon), HT-1080 (sarcoma), KB (human oral epidermoid carcinoma), LNCaP (prostate), LU-1 (lung), MEL-2 (melanoma), U373 (glioma) and ZR-75-1 (hormone-dependent breast).

TABLE 1

Cytotoxic Activity Profile of the Crude Ethyl Acetate Extract Obtained from Ziziphus mauritiana, Betulinic acid, Other Antineoplastic Agents
$ED_{50}$ (μg/ml)

| Compound | A431 | BC-1 | COL-2 | HT-1080 | KB | LNCaP | LU-1 | MEL-2 | U373 | ZR 75-1 |
|---|---|---|---|---|---|---|---|---|---|---|
| Ziziphus mauritiana crude extract | >20 | >20 | >20 | 9.5 | >20 | >20 | 5.2 | 3.7 | >20 | 15.8 |
| Betulinic acid | >20 | >20 | >20 | >20 | >20 | >20 | >20 | 2.0 | >20 | >20 |
| Taxol | 0.00 | 0.02 | 0.02 | 0.00 | 0.02 | 0.02 | 0.00 | 0.06 | 0.008 | 0.02 |
| Camptothecin | 0.00 | 0.07 | 0.005 | 0.01 | 0.00 | 0.006 | 0.00 | 0.02 | 0.000 | 0.001 |
| Ellipticine | 0.5 | 0.2 | 0.3 | 1.8 | 0.04 | 0.8 | 0.02 | 0.9 | 1.6 | 0.9 |
| Homoharringtonine | 0.02 | 0.03 | 0.1 | 0.01 | 0.00 | 0.03 | 0.03 | 0.04 | 0.2 | 0.06 |
| Mithramycin A | 0.09 | 0.3 | 0.06 | 1.5 | 0.09 | 0.05 | 0.2 | 1.2 | 0.04 | 0.2 |
| Podophyllotoxin | 0.03 | 0.03 | 0.005 | 0.00 | 0.08 | 0.04 | 0.00 | 0.003 | 0.004 | 0.4 |
| Vinblastine | 0.05 | 0.06 | 0.01 | 0.02 | 0.04 | 0.1 | 0.02 | 0.01 | 1.1 | 0.3 |
| Vincristine | 0.01 | 0.01 | 0.02 | 0.02 | 0.00 | 0.1 | 0.05 | 0.02 | 0.06 | 0.4 |

When using the test method used to develop the data in Table 1 (i.e., Method A), the greatest cytotoxic activity in response to betulinic acid was observed against human melanoma cells. Based on the data summarized in Table 1, in vivo studies using betulinic acid were performed. However, as set forth in Table 2, when betulinic acid was tested for cytotoxicity against cancer cell lines using other tests (i.e., Methods B and C), appreciable activity also was observed against other human cancer cell types (e.g., breast, sarcoma, lung, colon, squamous cell, prostate, and glioma). However, the greatest activity was observed against human melanoma cells. As discussed in detail hereafter, betulinic acid also showed excellent cytotoxic activity against human neuroblastoma cell lines.

Betulinic acid (1) has the structural formula:

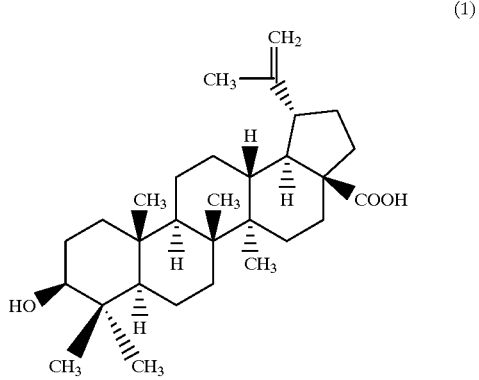

(1)

Betulinic acid is fairly widespread in the plant kingdom, and, as a frequently encountered compound, some previous biological activities have been reported.

Betulinic acid was obtained by extracting a sample of air-dried, milled stem bark (450 g) of Z. mauritiana with 80% aqueous methanol. The aqueous methanol extract then was partitioned successively with hexane and ethyl acetate to provide hexane, ethyl acetate and aqueous extracts. Among these extracts, the ethyl acetate (13.5 g) extract showed cytotoxic activity against a cultured melanoma cell line (MEL-2) with an $ED_{50}$ of 3.7 μg/ml. The ethyl acetate extract was chromatographed on a silica gel column using hexane-ethyl acetate (4:1 to 1:4) as eluent to give 10 fractions. Fractions 3 and 4 were combined and subjected to further fractionation to afford an active fraction (fraction 16) showing a major single spot by thin-layer chromatography [$R_f$ 0.67:CHCl$_3$:MeOH (chloroform:methanol) (10:1)], which yielded 72 mg of colorless needles after repeated crystallization from methanol (overall yield from dried plant material: 0.016% w/w).

The isolated active compound, betulinic acid ($ED_{50}$ of 2.0 μg/ml for MEL-2), has a molecular formula of $C_{30}H_{48}O_3$, as determined by high-resolution mass spectral analysis, a melting point range of 292–293° C. (decomposition). The literature melting point range for betulinic acid is 290–293° C. A mixed melting point range with a known sample of betulinic acid was not depressed. The optical rotation of the compound was measured as +7.3° (c=1.2; pyridine) (lit. +7.5°). The identity of the isolated compound as betulinic acid was confirmed by comparing the above physical properties, as well as $^1$H-nmr, $^{13}$C-nmr and mass spectral data of the isolated compound, with physical data and spectra of a known sample of betulinic acid as reported in the literature.

As illustrated by the data summarized in Table 1, betulinic acid has been reported as noncytotoxic with respect to cultured KB cells. Cytotoxicity of the crude extracts and purified compounds was determined in a number of cultured human cancer cell lines. Table 1 sets forth the various types of cancer cells evaluated using Method A. The cells were cultured in appropriate media and under standard conditions. To maintain logarithmic growth, the media were changed 24 hours prior to cytotoxic assays. On the day of the assay, the cells were harvested by trypsinization, counted, diluted in media, and added to 96-well plates containing test compounds dissolved in DMSO; the final DMSO concentration was 0.05%.

Table 2 summarizes test data showing the cytotoxicity of betulinic acid using test samples dissolved in tissue culture media (Method B) or 5% aqueous bovine serum albumin (Method C). Methods B and C illustrate the cytotoxicity of betulinic acid against cancer cell lines in addition to melanoma, particularly breast cancer, fibrosarcoma, lung cancer, colon cancer, epidermoid carcinoma, hormone-dependent breast cancer, and glioma.

In each of Methods A–C, the plates were incubated for three days. Following the incubation period, the cells were fixed and stained with sulforhodamine B (SRB) dye. The bound dye was liberated with Tris base, and the $OD_{515}$ was measured on an ELISA reader. The growth of the betulinic acid-treated cells was determined by the $OD_{515}$ values, and the growth was compared to the $OD_{515}$ values of treated control cells of Methods A–C. Dose response studies were performed to generate $ED_{50}$ values.

TABLE 2

| Betulinic Acid | $ED_{50}$ (µg/ml) | | | | | | | | | | | |
|---|---|---|---|---|---|---|---|---|---|---|---|---|
| | BC1 | HT | Lu1 | Mel1 | Mel2 | Mel4 | Col2 | KB | A431 | LNCaP | ZA-75-1 | U373 |
| Method A | >20 | >20 | >20 | 1.1 | 1.9 | 4.8 | 17.2 | 19.2 | >20 | >20 | >20 | >20 |
| Method B | 11.2 | 11.3 | 7.7 | 0.9 | 0.9 | 1.6 | 13.3 | >20 | 12.1 | 19.3 | 6.4 | 12.1 |
| Method C | 12.6 | 10.0 | NT | NT | 1.6 | NT | NT | 16.6 | >20 | 16.6 | 6.9 | 18.7 |

Sample dissolved in 10% DMSO (Method A), tissue culture media (Method B), or 5% aqueous bovine serum albumin (Method C); BC1, human breast cancer, HT, human fibrosarcoma; Lu1, human lung cancer; Mel1, Mel2, Mel4, human melanoma; Col2, human colon cancer; KB, human oral epidermoid carcinoma; A431, human epidermoid carcinoma; LNCaP, human prostate cancer; ZA-75-1, hormone-dependent human breast cancer; U373, human glioma; NT, not tested.

To test the in vivo ability of betulinic acid to serve as an antineoplastic agent against malignant melanoma, a series of studies was performed with athymic (nude) mice injected subcutaneously with human melanoma cells (MEL-2). The initial study investigated the activity of betulinic acid against unestablished tumors. Treatment with betulinic acid began on day 1, i.e., 24 hours, following tumor cell injection. At doses of 50, 250, and 500 mg/kg (milligram per kilogram) body weight, betulinic acid demonstrated effective inhibition of tumor growth with p values of 0.001 for each dose versus a control (FIG. 1). These results indicate that betulinic acid can be used to prevent melanoma by topical application of melanoma. Such a discovery is important for individuals who are predisposed to melanoma due to hereditary or environmental factors.

In particular, the data plotted in FIG. 1 was derived from experiments wherein four week old athymic mice were injected subcutaneously in the right flank with $3.0 \times 10^8$ UISO MEL-2 cells. UISO MEL-2 is a cell line derived from metastatic melanoma from human pleural fluid. Drug treatment was initiated on the day following tumor cell injection and continued every fourth day for a total of six doses. Four control animals received 0.5 ml intraperitoneal (IP) of PVP control solution, while treated animals (4 per group) received 50, 250, or 500 mg/kg/dose IP betulinic acid/PVP in deionized $H_2O$. Betulinic acid was coprecipitated with PVP to increase solubility and bioavailability. The mice were weighed, and the tumors measured with a micrometer every other day throughout the study. All animals were sacrificed and autopsied on day 33, when the mean tumor volume in the control animals was approximately one $cm^3$.

There was greater inhibition of tumor growth at the highest dose of betulinic acid versus the lowest dose (p=0.04). Toxicity was not associated with the betulinic acid treatment because toxicity is indicated by loss of body weight or other forms of acute toxicity. No weight loss was observed.

Figure 2:
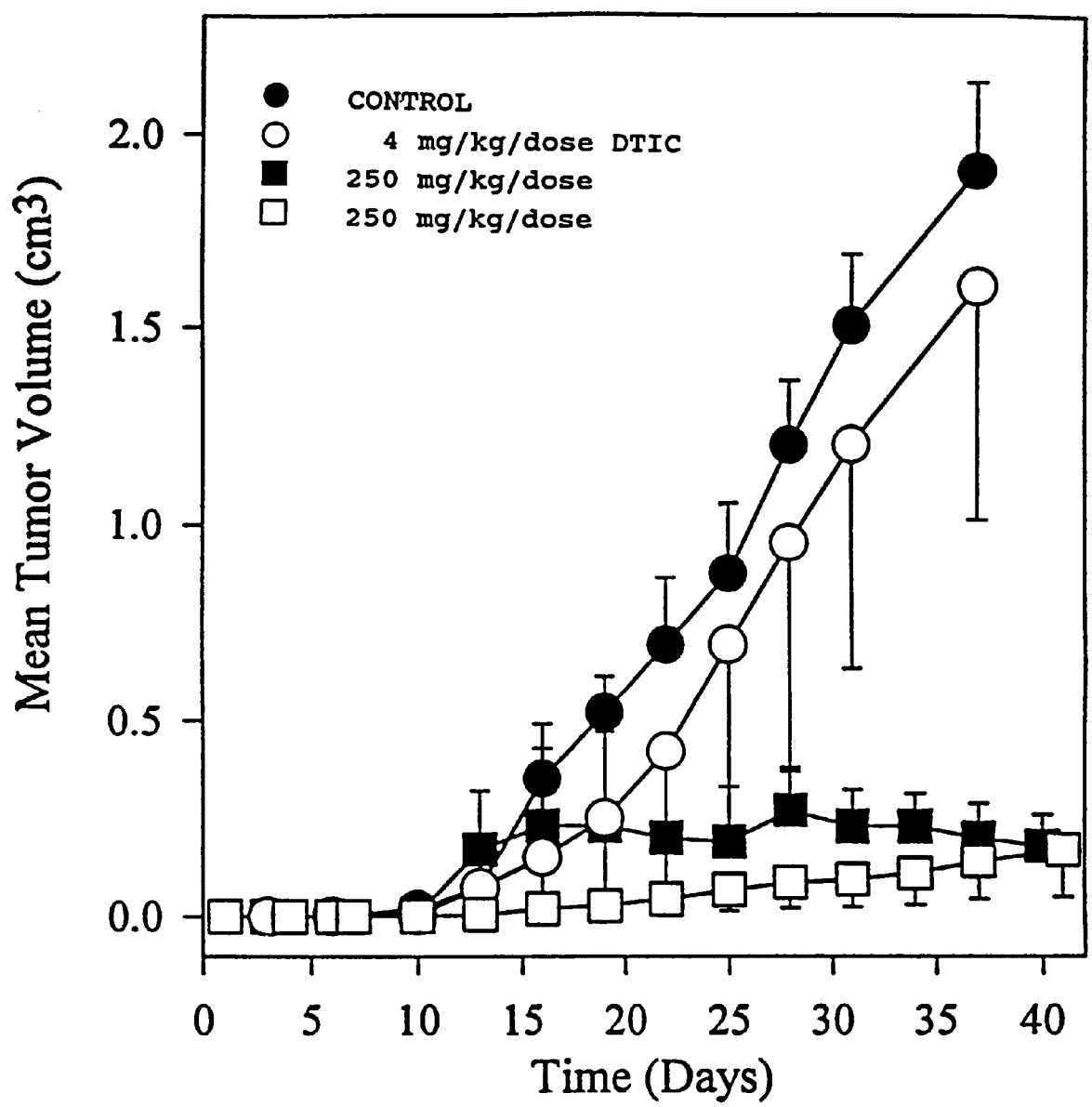
FIG. 2 is a plot of mean tumor volume (in $cm^3$) vs. time for established MEL-2 tumors in control mice and mice treated with DTIC or betulinic acid.

Next, in vivo testing of betulinic acid was performed on established melanomas. In this study, treatment was withheld until day 13, by which time a palpable tumor mass was present in all mice. As illustrated in FIG. 2, under these conditions betulinic acid successfully abrogated tumor growth (p=0.0001). Furthermore, tumor growth did not parallel that of the control (untreated) group even 14 days after the termination of treatment.

In particular, with respect to FIG. 2, four-week-old athymic mice were injected with $5 \times 10^8$ MEL-2 cells subcutaneously in the right flank. Four treatment groups of five mice each were studied. In one group, the mice received 250 mg/kg/dose of IP betulinic acid/PVP every third day for six total doses initiated the day following tumor cell injection. The control group received 0.5 ml IP saline. A DTIC treatment group received 4 mg/kg/dose IP DTIC every third day from day 13 to day 28 of the study. The betulinic acid treatment group received 250 mg/kg/dose IP betulinic acid/PVP every third day from day 13 to day 27. The control and DTIC-treated mice were sacrificed and autopsied on day 36 due to their large tumor burden. The remaining mice were sacrificed and autopsied on day 41.

As illustrated in FIG. 2, the efficacy of betulinic acid also was compared to DTIC, which is clinically available for the treatment of metastatic melanoma. The dose of DTIC, which is limited by toxicity, was selected to be equivalent to that administered to human patients. Tumor growth in the betulinic acid-treated group was significantly less than that observed in the DTIC-treated animals (p=0.0001). Compared to controls, DTIC produced a significant, but less pronounced, reduction in tumor growth, with a p value of 0.01. A fourth group in this study was treated with a schedule similar to that in the initial study. Under these conditions, betulinic acid, as demonstrated before, significantly inhibited tumor development (p=0.0001) and caused a prolonged reduction in tumor growth of up to three weeks following treatment termination.

Figure 4:
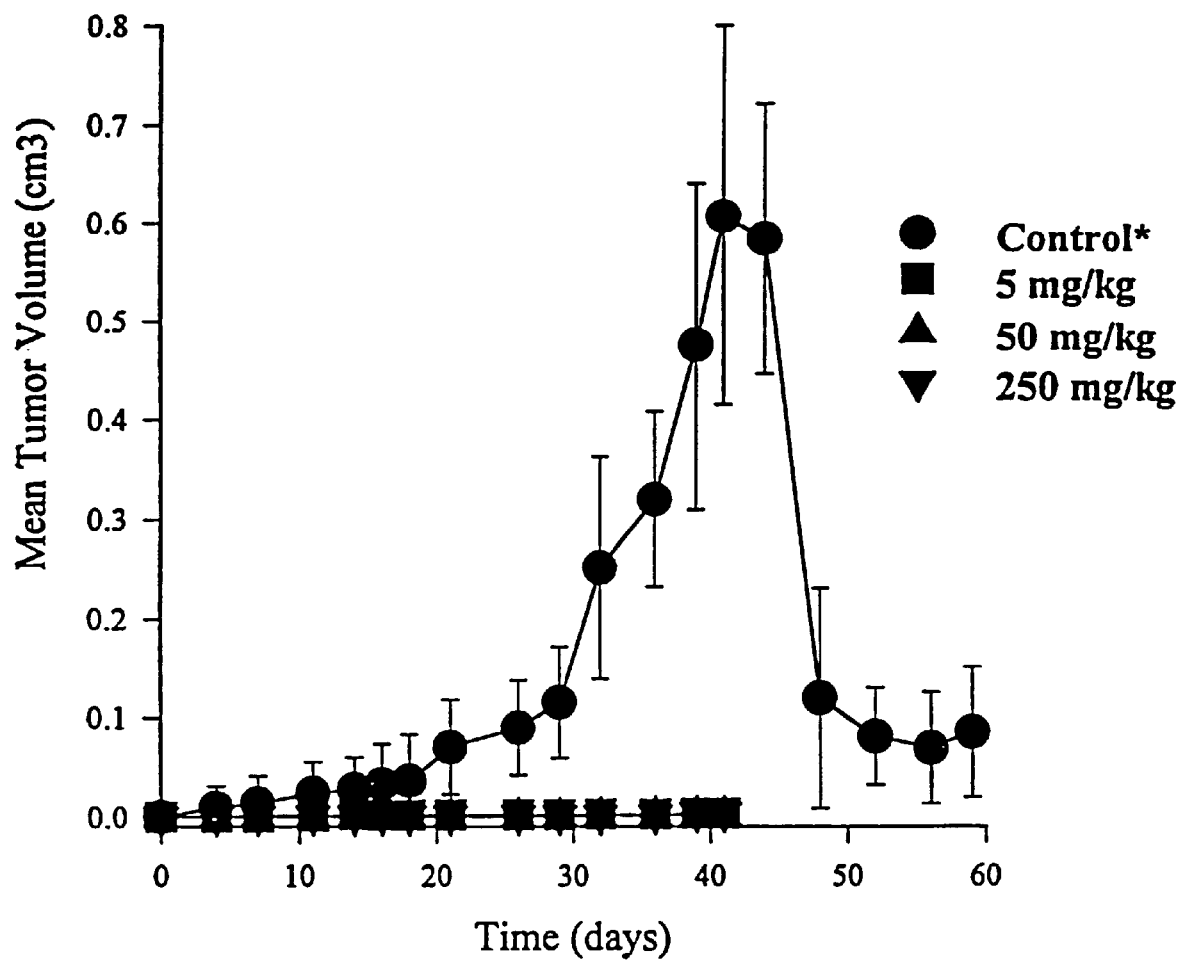
FIGS. 4 and 5 are plots of mean tumor volume ($cm^3$) vs. time for established and nonestablished MEL-1 tumors in control mice and mice treated with increasing doses of betulinic acid.
Figure 5:
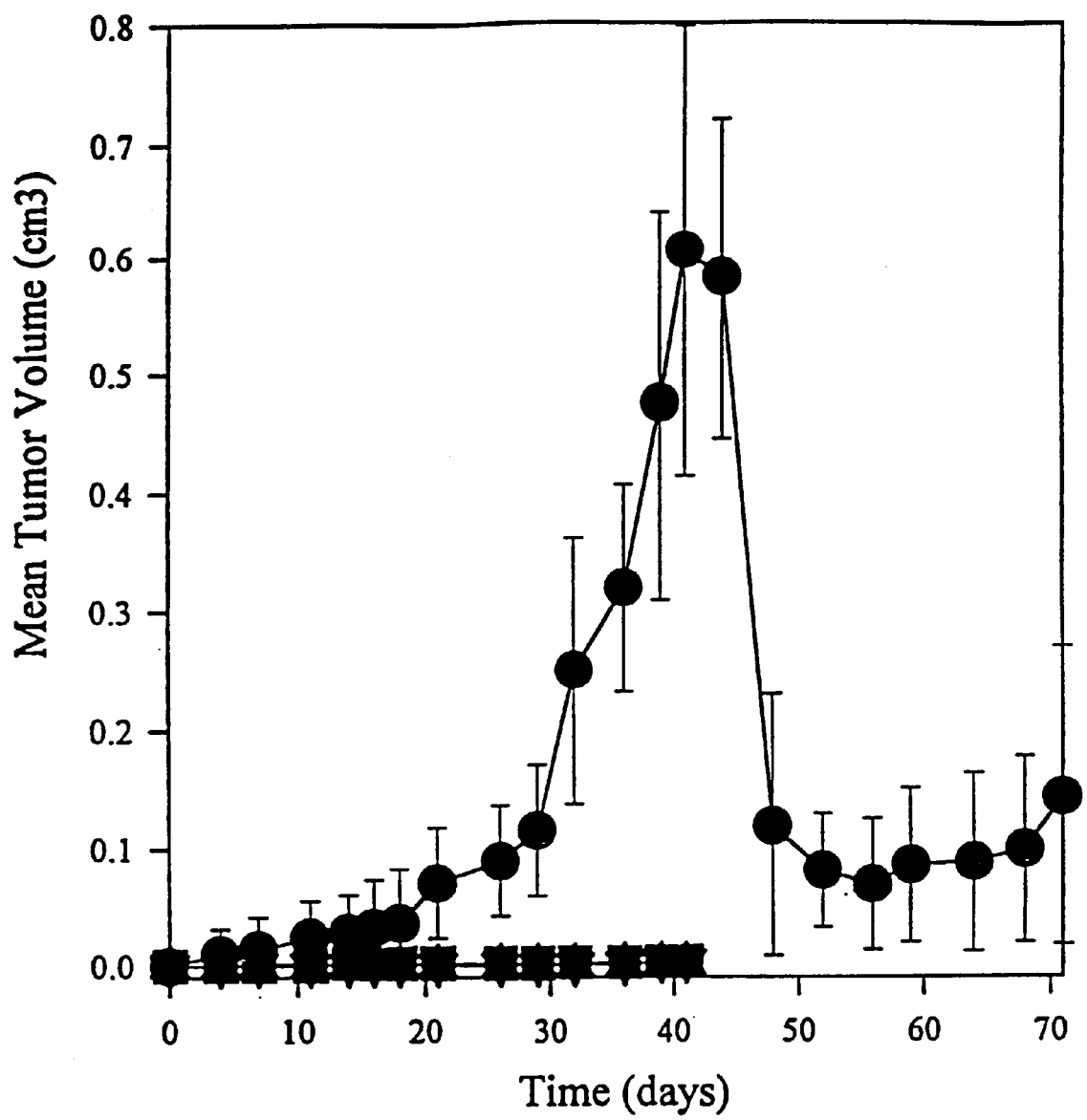

FIGS. 4 and 5 illustrate that betulinic acid also showed activity against MEL-1 cells. In particular, with respect to FIGS. 4 and 5, four week old athymic mice were injected subcutaneously in the right flank with $5.0 \times 10^8$ UISO MEL-1 cells. Drug treatment was initiated on the day following tumor cell injection and continued every fourth day for a total of six doses. Four control animals received 0.5 ml intraperitoneal (IP) saline, while treated animals (4 per group) received 5, 50 or 250 mg/kg/dose IP betulinic acid/PVP in dd $H_2O$. The mice were weighed, and tumors were measured with a micrometer every third day throughout the study. Treated animals were sacrificed and autopsied on day 41, when the mean tumor volume in the control mice was approximately 0.5 $cm^3$. The control mice then received six doses of 50 mg/kg every fourth day beginning day 41 and were sacrificed and autopsied on day 71.

The results illustrated in FIGS. 4 and 5 with respect to MEL-1 cells were similar to the results illustrated in FIGS. 1 and 2. Betulinic acid therefore is active both against MEL-1 and MEL-2 cells.

The mechanism by which antitumor agents mediated their activity is of great theoretical and clinical importance. Therefore, the mode of action by which betulinic acid mediates the melanoma-specific effect was investigated. Visual inspection of melanoma cells treated with betulinic acid revealed numerous surface blebs. This observation, as opposed to cellular membrane collapse, suggested the induction of apoptosis.

Apoptosis is the cellular process whereby cell death occurs in a selective and developmentally regulated manner. The process is involved in embryo-logic molding, normal cell turnover, immune regulation, and hormone-dependent atrophy. Tumor cell death can occur by necrosis or apoptosis, and these processes are separate and distinct. Necrosis occurs secondary to hypoxia or exposure to exogenous cytotoxic agents. Programmed cell death results from signals generated internal to the eukaryotic organism. The induction, or triggering, of programmed cell death is commonly developmentally regulated and results in the removal of unnecessary, overabundant, or superfluous cells. Apoptosis has euphemistically been name "altruist suicide" in that cells receiving the signals to die obediently do so.

One of the most common molecular and cellular anatomical markers of apoptosis is the formation of "DNA ladders," which correspond to the products of random endonucleolytic digestion of inter-nucleosomal DNA. Although recent studies have shown that a lack of DNA laddering does not necessarily indicate a failure to undergo apoptosis, double-strand DNA scission that yields a fragment of about 50 kilobase pairs (Kbp) has been shown to consistently correlate with induction of apoptosis by various treatments in a variety of cell lines. Thus, generation of the 50 Kbp fragment is a reliable and general indicator of apoptosis. Generation of the fragment occurs upstream of the process leading to DNA ladders and represents a key early step in the commitment to apoptosis.

Therefore, an important feature of the present invention is a method of analyzing and quantifying the formation of the 50 Kbp fragment as a biomarker for induction of apoptosis in human cancer cell lines. This method comprises treatment of cells in culture, followed by analysis of the total cellular DNA content using agarose field-inversion gel electrophoresis. Under these conditions, the 50 Kbp fragment is resolved as a diffuse band. The fraction of the total cellular DNA represented by the 50 Kbp fragment is determined by densitometry on the contour of this band.

To investigate the ability of betulinic acid to induce apoptosis, the above-described method was adapted for use with the MEL-2 cell line. As shown in FIG. 3A, time-dependent formation of a 50 Kbp DNA fragment was induced by betulinic acid with MEL-2 cells. Induction was at a maximum after a 56 hour treatment period. After this time period, a decline in the relative amount of the 50 Kbp fragment was observed, probably due to internal degradation. Also observed in the agarose gel were DNA fragments of about 146 and about 194 Kbp, which are theorized to be precursors in the process leading to the formation of the 50 Kbp fragment. Additionally, the induction of apoptosis (50 Kbp fragment) mediated by betulinic acid was dose-dependent (FIG. 3B), and the $ED_{50}$ value (about 1.5 $\mu$g/ml) observed in the apoptotic response closely approximated the $ED_{50}$ value previously determined for the cytotoxic response (Table 1).

With further respect to FIG. 3A, cultured MEL-2 cells ($10^6$ cells inoculated per 25 $cm^2$ flask) were treated with 2 g/ml betulinic acid (200 $\mu$g/ml DMSO, diluted 1:100 in media) for 24, 32, 48, 56 and 72 hours. After the treatment, the cells were harvested, collected by centrifugation, then snap frozen in liquid nitrogen for subsequent analysis. Samples were analyzed on a 1% agarose gel in a Hoefer HE100 SuperSub apparatus cooled to 10° C. by a circulating water bath. The electrode buffer was 0.5× TBE buffer containing 0.25 $\mu$g/ml ethidium bromide and was circulated during electrophoresis. Each gel included 20 $\mu$L Sigma Pulse Marker 0.1–200 Kbp DNA size markers. Prior to sample loading, 50 $\mu$L 2% SDS was added to each sample well. Each sample tube was rapidly thawed, then the pelleted cells were immediately transferred in a volume about 50 $\mu$L to the well containing SDS. Each well then was overlaid with molten LMP agarose, which was allowed to gel prior to placing the gel tray in the SuperSub apparatus.

Electrophoresis was performed at 172 volts for a total of 18 hours using two sequential field inversion programs with pulse ramping. The DNA/ethidium bromide fluorescence was excited on a UV transilluminator and photographed using Polaroid type 55 P/N film. The negative was analyzed using a PDI scanning densitometer and Quantity One software. The intensity of the 50 Kbp fragment was determined by measuring the contour optical density (OD×mm$^2$) as a percent of the total optical density in the sample lane, including the sample well. The decrease in the 50 Kbp band definition caused by internal degradation, and does not represent a reversal of the process.

Figure 3B:
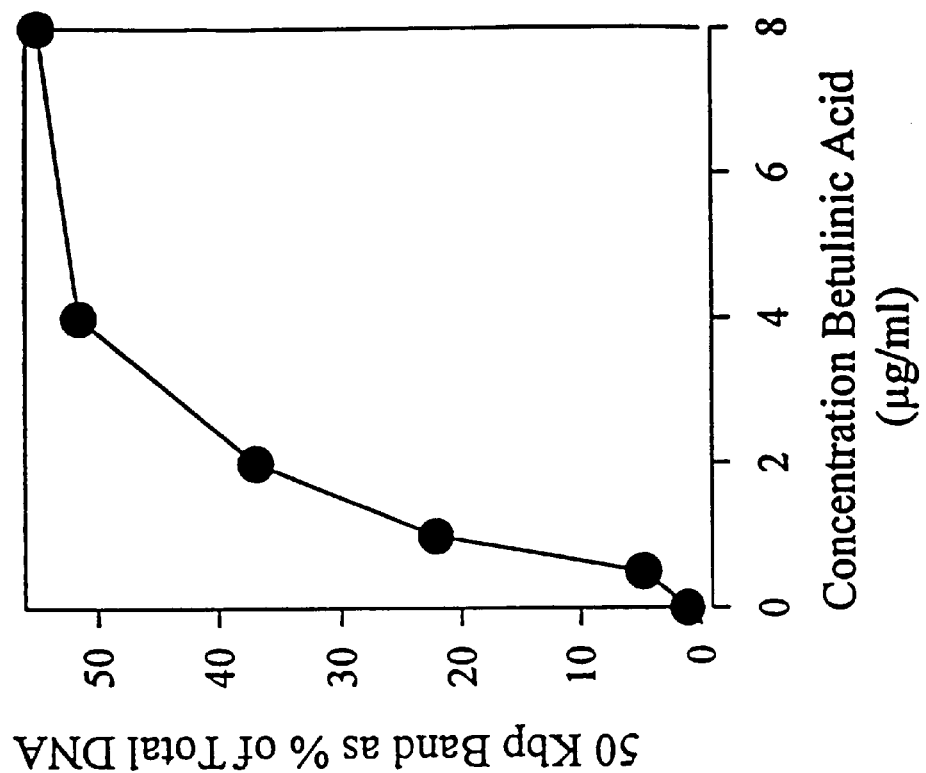
FIG. 3(B) is a plot of the 50 Kbp band as % total DNA versus concentration of betulinic acid (µg/ml)
Figure 3A:
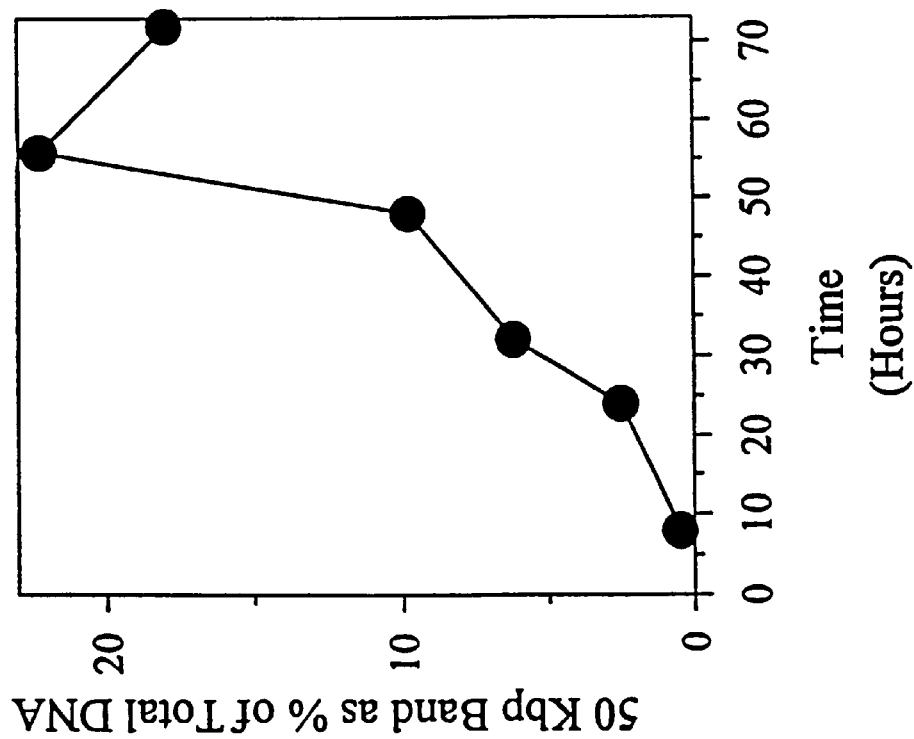
FIG. 3(A) is a plot of the 50 Kbp (kilobase pairs) band as % total DNA v. time for treatment of MEL-2 cells with 2 µg/ml (micrograms per milliliter) betulinic acid.

With further respect to FIG. 3B, cultured MEL-2 cells were treated for 56 hours with the following concentrations of betulinic acid: 0, 0.1, 1.0, 2.0, 4.0 and 8.0 $\mu$g/ml. The cells were harvested and apoptosis measured as described for FIG. 3A. The experiment was repeated and a similar dose-response curve was observed (data not shown).

These data suggest a causal relationship, and it is theorized that betulinic acid-mediated apoptosis is responsible for the antitumor effect observed with athymic mice. Time-course experiments with human lymphocytes treated in the same manner with betulinic acid at concentrations of 2 and 20 $\mu$g/ml did not demonstrate formation of the 50 Kbp fragment (data not shown) indicating the specificity and possible safety of the test compound.

Taking into account a unique in vitro cytotoxicity profile, a significant in vivo activity, and mode of action, betulinic acid is an exceptionally attractive compound for treating human melanoma. Betulinic acid also is relatively innocuous toxicity-wise, as evidenced by repeatedly administering 500 mg/kg doses of betulinic acid without causing acute signs of toxicity or a decrease in body weight. Betulinic acid was previously found to be inactive in a Hippocratic screen at 200 and 400 mg/kg doses.

Betulinic acid also does not suffer from the drawback of scarcity. Betulinic acid is a common triterpene available from many species throughout the plant kingdom. More importantly, a betulinic acid analog, betulin, is the major constituent of white-barked birch species (up to 22% yield), and betulin can be converted to betulinic acid.

It also has been found that betulinic acid induces apoptosis in human neuroblastoma cell lines, and, therefore, can serve as a compound to inhibit and treat neuroblastomas. In general, apoptosis can be a path by which neuroblastoma (NB) spontaneously regresses in certain clinical situations. Neuroblastoma has long been recognized to show spontaneous regression during fetal development, and in the majority of stage 4s infants less than 1 year of age with disseminated disease. The stage IVs disease regresses with no chemotherapy in 50% of the patients.

The mechanism by which this occurs is not completely understood, but has been theorized as programmed cell death or apoptosis. The ability of betulinic acid to induce apoptosis in human melanoma, with in vitro and in vivo model systems, has been discussed above. Melanoma, like neuroblastoma, is derived from the neural crest cell. Therefore, it has been theorized that neuroblastoma cells have the machinery for programmed cell death, and that apoptosis could be induced by betulinic acid.

The effect of betulinic acid on NB cells based upon: (a) the above melanoma data, (b) the neural crest origin of MEL and neuroblastoma, and the potential for NB cells to undergo apoptosis were examined. Nine human neuroblastoma cell lines were treated in vitro with betulinic acid at concentrations of 0 to about 20 µg/ml for 0–6 days. Profound morphologic changes were noted within 3 days. In particular, the cells withdrew their axonic-like extensions, became nonadherent, and condensed into irregular dense spheroids typical of apoptotic cell death ($ED_{50}$=14–17 µg/ml). DNA fragmentation analysis showed ladder formation in the 100–1200 bp region in 3/3 neuroblastoma cell lines treated with betulinic acid for 24–72 hours. Betulinic acid, therefore, induces apoptosis in neuroblastoma in vitro. No nonspecific toxicities or adverse effects were observed.

Neuroblastoma is the most common solid tumor in early childhood and develops in the adrenal medulla or sympathetic ganglia. Introduction of aggressive combination chemotherapy protocols has increased the survival rates for many forms of childhood neoplasms, including, for example, acute leukemia, Wilm's Tumor, and osteosarcoma. However, advanced stage neuroblastoma remains intractable to chemotherapy. Neuroblastoma has a particularly poor prognosis (i.e., less than 30% survival) in patients over 2 years of age, advanced stage disease, and/or disease characterized by N-myc gene amplification. N-myc is an oncogene which has a developmentally dependent pattern of expression limited to embryonic and fetal development. Expression of N-myc is not detectable in mature normal tissues. N-myc amplification in neuroblastoma tumor cells confers a poor prognosis independent of age and stage.

By contrast, low stage neuroblastoma patients diagnosed at less than 2 years, and those tumors with a single copy of N-myc, are cured greater than 75% of the time. Furthermore, there is also a unique advanced stage neuroblastoma which occurs in infants less than 1 year of age, i.e., stage IV-S, that shows a remarkably high spontaneous regression rate of nearly 100 times that of any other human cancer. This suggests that at least one form of neuroblastoma can exhibit a delayed onset of apoptosis by a mechanism that remains to be defined.

Recently, the expression of several genes, including N-myc, has been associated with the induction or suppression of apoptosis. Expression of bcl-2 (and the related gene bcl-x) correlates with suppression of apoptosis. Overexpression of bcl-2 and bcl-x correlates with overexpression of N-myc and modulates chemotherapy-induced apoptosis, possibly through interaction with the multidrug resistance-associated protein gene MRP (multidrug resistant protein). MRP is expressed in poor prognosis neuroblastoma, which also exhibits overexpression of N-myc. While bcl-2 suppresses apoptosis, its heterodimeric partner, bax, accelerates apoptosis, and its homologue bak counteracts the bcl-2-suppressed apoptosis machinery. Both bcl-2 and myc appear to be under the regulation of the tumor suppressor p53.

Several anticancer drugs appear to act by induction of apoptosis. As discussed above, betulinic acid induces apoptosis in cultured melanoma cells, and caused nearly complete regression of human melanoma tumors carried in athymic mice. This finding is in contrast to the few prior reports of the tumor-inhibitory properties of betulinic acid, and which, at most, suggest only marginal effectiveness. The results of many of the early betulinic acid studies were refuted in subsequent studies. The $ED_{50}$ for betulinic acid against melanoma cells in culture was about 1.1 to about 4.8 µg/ml. Betulinic acid exhibited no toxicity in athymic mice at 500 mg/kg body weight (approximately 35 g per treatment for the average person). Betulinic acid is an excellent antineoplastic agent because it has little nonspecific toxicity and high specific toxicity for neoplasms, and because it triggers selective programmed cell death in tumor cells.

As set forth below, neuroblastoma cells have a functional programmed cell death machinery, and apoptosis can be induced by betulinic acid. These conclusions are based upon the following observations: (a) neuroblastoma and melanoma share a common neural crest cell origin, (b) stage IVs neuroblastoma exhibits apparent spontaneous apoptotic regression, and (c) betulinic acid induced apoptosis in vitro and in vivo in melanoma.

The materials and methods used to test the ability of betulinic acid to induce apoptosis in neuroblastoma were as follows.

Established human neuroblastoma cell lines were utilized. N-myc amplified (LAN-5; IMR-5; and NBL-W, and the corresponding cell line NBL-WR, established at the time of relapse) cell lines and nonamplified (SKNSH and SHSY5Y) cell lines, as well as the single-copy N-myc cell line NBL-S with increased N-myc protein expression were used. In addition, two antisense N-myc RNA expressing neuroblastoma cell lines (NBAS 5 and NBAS 6) derived from NBL-S cells also were included in the study. These cell lines are unique in that N-myc protein expression has been downregulated by 50% resulting in decreased clonogenicity in soft agar. All cell lines were maintained in cell culture at 5% carbon dioxide ($CO_2$), 37° C., in RPMI-1640 media with 10% fetal calf serum, and additives including penicillin-streptomycin, amphotericin B, and glutamine.

Light Microscopy: $1 \times 10^5$ neuroblastoma cells were plated into 24 well plates. The cells were treated with betulinic acid at 0, 1, 3, 6, 10, and 20 µg/ml betulinic acid for six days. The effect of betulinic acid treatment on detachment and accumulation of free floating, nonadherent cells was recorded.

Sulforhodamine B Assay: $ED_{50}$ values resulting from betulinic acid treatments were measured by the sulphorhodamine (SRB) dye liberation technique. Four neuroblastoma cell lines (SKNSH, IMR-5, NBL-S, and LAN-5) were treated with betulinic acid at concentrations of 0, 6, and 20 µg/ml. The cells were collected at 0, 6, 24, and 48 hours after initiation of betulinic acid treatment. Cells were fixed with 50% trichloracetic acid (at 4° C.) and stained with 0.4% SRB in 1% acetic acid. The bound SRB was released with 0.1M Tris base and the absorbance measured at $A_{570}$. Results were reported as an "inhibition rate" ((1-Treatment/Control)× 100%).

Propidium Iodide Assay: Detection of apoptotic cells was determined by the modified propidium iodide technique of R. D. Jacobson et al., Nature, 361 (1993), pages 365–369. Three neuroblastoma cell lines (SKNSH, IMR-5, and LAN-5) were treated with betulinic acid at 0, 6, and 20 µg/ml for 0, 6, 24, and 48 hours and collected by standard technique. The cells ($5 \times 10^5$) were centrifuged at low speed (400×g) for 10 minutes, then rinsed in potassium chloride (KCl) (75 mM) for 10 minutes. The cells were pelleted and treated twice with methanol/acetic acid (MeOH/AcH) (3:1) for 15 minutes and pelleted. Cells were affixed to slides and air dried for 72 hours. Slides were incubated with 0.05 µg/ml propidium iodide in phosphate buffered saline (PBS) and 100 µg/ml RNase A for 30 minutes in the dark and examined by fluorescent microsopy.

DNA Fragmentation: Internucleosomal fragmentation forms integer multiples of 180–200 bp fragments. A $Ca^{2+}$-dependent endonuclease cleaves internucleosomal linker DNA to the size of DNA wrapped around a single histone octamer. This degradation pattern can be observed as a DNA ladder using standard agarose gel electrophoresis. Three neuroblastoma cell lines (SKNSH, IMR-5, and LAN-5) were examined for internucleosomal fragmentation after treatment with betulinic at 20 μg/ml and collected at 0, 6, 24, and 48 hours after initiation of betulinic acid treatment. The method of M. K. Ritke et al., *Mol. Pharmacol.*, 46 (1994), pages 605–611, was utilized to visualize DNA fragmentation. After in vitro treatment with betulinic acid, approximately $2 \times 10^6$ cells were pelleted by low speed (about 100 times gravity) centrifugation for 5 minutes. The cells were washed with normal saline (0.85% NaCl), then solubilized for 1 hour at 50° C. in lysis buffer (20 μl/cell pellet; 50 mM Tris-HCl, 10 mM EDTA, 0.5% sodium lauryl sarcosine, 10 μg proteinase K, pH 8.0). RNase A was added (10 μl at 0.5 mg/ml) after initial lysis (1 hour) and incubated for 1 hour at 50° C. Proteolysis and RNA degradation was terminated by raising the sample temperature to 70° C. for 5 minutes. Agarose gels (2% w/v) prepared and run with TBE buffer were used for DNA fragmentation visualization. Samples were loaded into the wells by preparing 1% agarose plugs and were run at 40 V overnight (room temperature). The neuroblastoma cell lines were compared to HT1080 human sarcoma cells and Mel-2 melanoma cells under the described conditions.

The results of these test methods are summarized below and in Table 3.

Light Microscopy: Initial investigation of betulinic acid for cytotoxic action on human neuroblastoma cell lines demonstrated classic apoptotis. A time course of six days with a concentration series of 1 to 20 μg/ml betulinic acid showed all nine neuroblastoma cell lines tested were sensitive to the cytotoxic action of betulinic acid, as set forth in Table 3. At the highest concentration tested (i.e., 20 μg/ml), all neuroblastoma cells were killed within 72 hours. After treatment with betulinic acid, neuroblastoma cells undergoing apoptosis exhibited a characteristic appearance. Adherent monolayer forming cells retracted their axonal-like extensions and detached. In comparison to untreated control cells, the treated cells became spheroid with exvaginations.

TABLE 3

Betulinic acid cytotoxicity in neuroblastoma cell lines
Betulinic acid treatment (μg/ml)

| Cell Lines | 1 | 3 | 6 | 10 | 20 |
|---|---|---|---|---|---|
| SKNSH | – | – | –/+ | ++ | ++++ |
| SHSY5Y | – | – | –/+ | +++ | ++++ |
| IMR-5 | – | –/+ | ++ | ++++ | ++++ |
| LAN-5 | – | + | ++ | +++ | ++++ |
| NBL-S | – | – | + | +++ | ++++ |
| NBAS5 | – | – | + | +++ | ++++ |
| NBAS6 | – | – | + | +++ | ++++ |
| NBL-W | – | – | +++ | +++ | ++++ |
| NBL-WR | – | – | + | ++ | ++++ |
| MEL-2 | – | +/– | + | ++ | ++++ |

Neuroblastoma cells ($1 \times 10^5$) were plated into 24 well plates and were treated with betulinic acid in standard culture medium for three days. The effect of betulinic acid on detachment and accumulation of free floating, nonadherent cells was recorded. A six-point scale was used with (–) for no observable cytotoxicity, (+/–) some possible but not clear-cut cytotoxicity, and a gradation form (+ to ++++) to indicate clearly observable cytotoxic effects with increasing numbers of invaginated, detached cells with increasing cell debris.

Sulforhodamine B Assay: SRB quantitation showed increased inhibition rates for both increased concentration of betulinic acid and increased time of exposure to betulinic acid. The $ED_{50}$ was about 14 to 17 μg/ml for a betulinic acid treatment time of 48 hours.

Propidium Iodide: Three human neuroblastoma cell lines (SKNSH, IMR-5, and LAN-5) were treated with betulinic acid at concentrations of 0, 6, and 20 μg/ml, and the cells were collected at 0 and 48 hours after initiation of betulinic acid treatment. At 20 μg/ml, the nuclei of a majority of the neuroblastoma cells were disrupted, and residual nuclear fragments were consistent with apoptotic bodies.

DNA Fragmentation Analysis: Based on micrographic observation, three cell lines were examined (i.e., SKNSH, IMR-5, LAN-5) for evidence of internucleosomal fragmentation. DNA fragmentation typical of apoptosis was evident after treatment with betulinic acid for 72 hours at 20 μg/ml in all three cell lines SKNSH showed the most distinct banding pattern.

The above-described morphological and biochemical analysis shows that betulinic acid induces apoptosis in neuroblastoma cells. Treatment with 10–20 μg/ml of betulinic acid resulted in greater than 90% cell death after 72 hours. Cytotoxicity studies demonstrated $ED_{50}$ values in the range of about 14–17 μg/ml at 48 hours. Light microscopic observations revealed axonic-like projections were retracted and propidium iodide staining revealed fragmentation of the nucleus after treatment with betulinic acid. Finally, molecular analysis of apoptosis was examined by DNA fragmentation and the DNA ladder characteristic of apoptosis was evident after treatment with betulinic acid on three different neuroblastoma cell lines.

The prognosis for advanced stage neuroblastoma in children greater than 2 years remains dismal despite multimodal aggressive therapy with an overall survival rate of less than 30%. Some anticancer agents, including vincristine, etoposide, and cisplatin, induce apoptosis. Each of these agents is frequently utilized in current protocols for the treatment of advanced stage neuroblastoma, however, all have significant nonspecific toxicities. Because further intensification of therapy can produce intolerable toxicities, alternative pharmacologic approaches having minimal nonspecific toxicities are desirable. Betulinic acid is cytotoxic to human neuroblastoma cells in vitro apparently by inducing apoptosis. Betulinic acid, therefore, is a useful anticancer agent because it induces apoptosis in susceptible cells, and has shown no nonspecific toxicities.

In addition to betulinic acid, betulinic acid derivatives can be used in a composition to treat, or inhibit, tumor growth. Betulinic acid derivatives include, but are not limited to esters of betulinic acid, such as betulinic acid esterified with an alcohol having one to sixteen, and preferably one to six, carbon atoms, or amides of betulinic acid, such as betulinic acid reacted with ammonia or a primary or secondary amine having alkyl groups containing one to ten, and preferably one to six, carbon atoms.

Another betulinic acid derivative is a salt of betulinic acid. Exemplary, but nonlimiting, betulinic acid salts include an alkali metal salt, like a sodium or potassium salt; an alkaline earth metal salt, like a calcium or magnesium salt; an ammonium or alkylammonium salt, wherein the alkylammonium cation has one to three alkyl groups and each alkyl group independently has one to four carbon atoms; or transition metal salt.

Other betulinic acid derivatives also can be used in the composition and method of the present invention. One other derivative is the aldehyde corresponding to betulinic acid or betulin. Another derivative is acetylated betulinic acid, wherein an acetyl group is positioned at the hydroxyl group of betulinic acid.

In particular, betulinic acid derivatives have been synthesized and evaluated biologically to illustrate that betulinic acid derivatives possess selective antitumor activity against cancer cell lines. It has been demonstrated that modifying the parent structure of betulinic acid provides numerous betulinic acid derivatives that can be developed as antitumor drugs, especially with respect to human melanoma and neuroblastoma. The ability of betulinic acid derivatives to demonstrate antitumor activity is important because betulinic acid, although possessing antitumor activity, also possesses a poor water solubility. Therefore, the low water solubility of betulinic acid can be overcome by providing an appropriate derivative of betulinic acid. Modifying the parent structure betulinic acid structure also can further improve antitumor activity against various cancer cells.

An examination of the structure of betulinic acid, i.e., compound (1), reveals that betulinic acid contains three positions, i.e., the C-3, C-20, and C-28 positions, where functional groups can be introduced. In addition, the introduced functional groups, if desired, then can be modified. Through a series of reactions at these three positions, a large number of betulinic acid derivatives were prepared and evaluated for bioefficacy against a series of human tumor cell lines, especially against human melanoma cell lines.

With respect to modifications at the C-3 position of betulinic acid, the hydroxyl group at the C-3 position can be converted to a carbonyl group by an oxidation reaction. The resulting compound is betulonic acid, i.e., compound (2). The ketone functionality of betulonic acid can be converted to oxime (3) by standard synthetic procedures. Furthermore, a large number of derivatives (4) can be prepared through substitution reactions performed on the hydroxyl group of oxime (3), with electrophiles, as set forth in equation (a):

wherein $R_a$=H or $C_1$–$C_{16}$ alkyl, or $R_a$=$COC_6H_4X$, wherein X=H, F, Cl, Br, I, $NO_2$, $CH_3$, or $OCH_3$, or $R_a$=$COCH_2Y$, wherein Y=H, F, Cl, Br, or I, or $R_a$=$CH_2CHCH_2$ or $CH_2CCR_1$, wherein $R_1$ is H or $C_1$–$C_6$ alkyl. When $R_a$ is $C_1$–$C_{16}$ alkyl, preferred alkyl groups are $C_1$–$C_6$ alkyl groups.

The ketone functionality of betulonic acid can undergo a reductive amination reaction with various aliphatic and aromatic amines in the presence of sodium cyanoborohydride ($NaBH_3CN$) to provide the corresponding substituted amines (5) at the C-3 position, as set forth in equation (b).

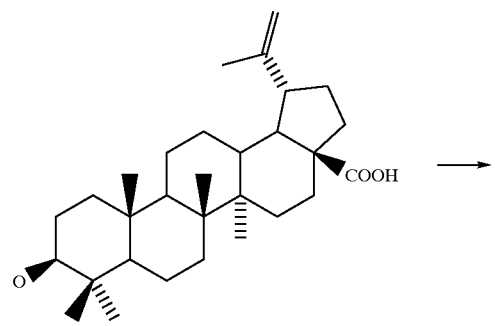

(b)

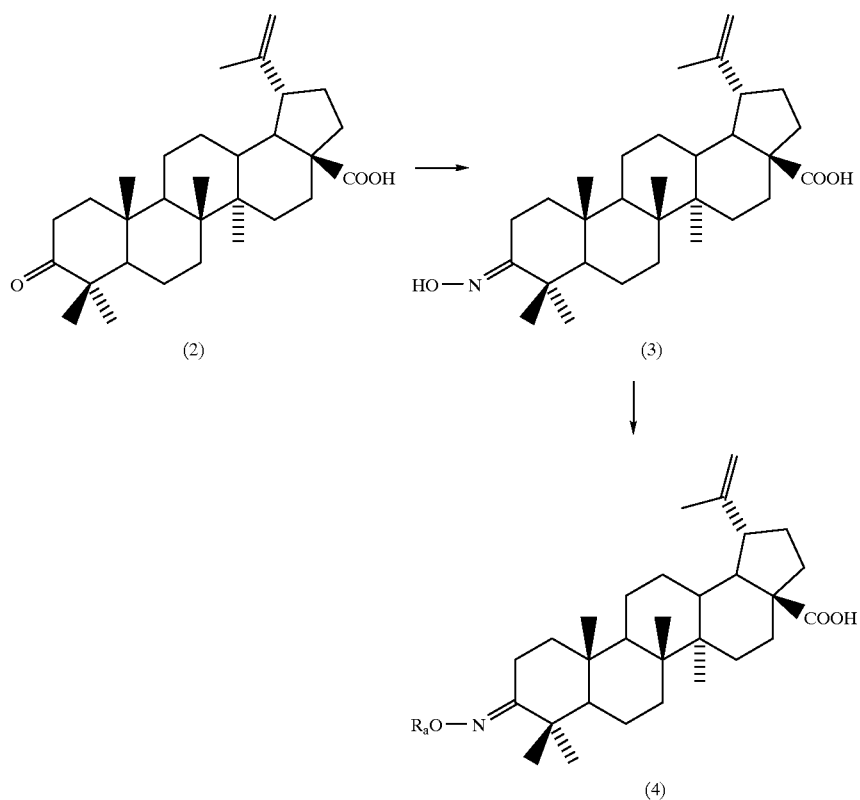

(a)

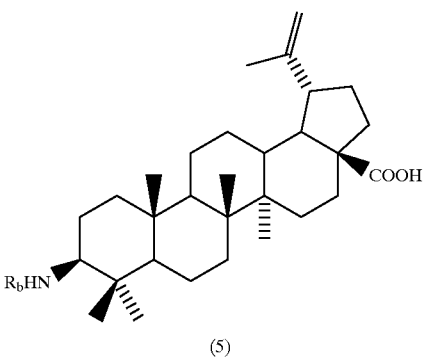

(5)

wherein $R_b$=H or $C_1$–$C_{10}$ alkyl, or $R_b$=$C_6H_4X$. A primary amine derivative, i.e., $R_b$=H, at the C-3 position can be reacted with a series of acyl chlorides or anhydrides, or alkyl halides, to provide amides and secondary amines (6), respectively, as set forth in equation (c).

(c)

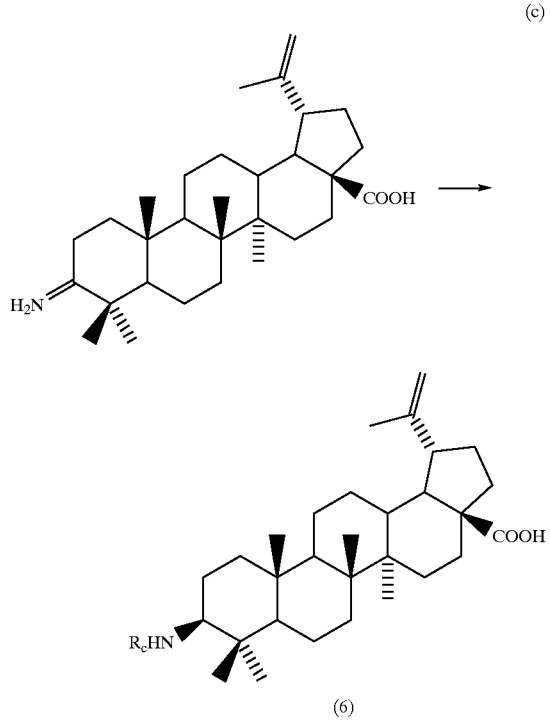

(6)

wherein $R_c$=$COC_6H_4X$, or $R_c$=$COCH_2Y$, or $R_c$=$CH_2CHCH_2$ or $CH_2CCR_1$.

The ketone functionality of betulonic acid can react with a series of lithium acetylides (i.e., LiC≡$CR_1$) to provide alkynyl alcohol derivatives (7) at the C-3 position. Based on the chemical reactivity and the stereoselectivity of the betulonic acid structure, α-alkynyl substituted β-hydroxyl alkynyl betulinic acid are the major products of the reaction, as set forth in equation (d).

(d)

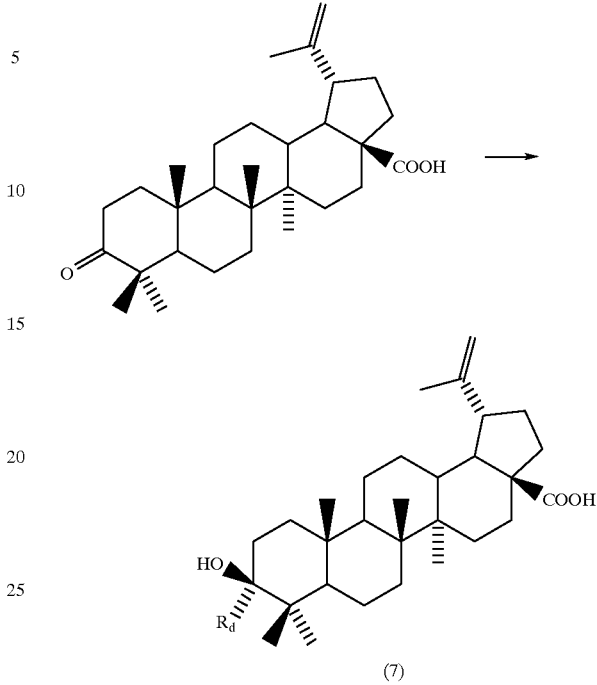

(7)

wherein $R_d$=$CCR_1$, wherein $R_1$, is H or $C_1$–$C_6$ alkyl.

A number of esters also can be prepared by reacting the hydroxyl group of betulinic acid with a variety of acyl chlorides or anhydrides (8), as set forth in equation (e).

(e)

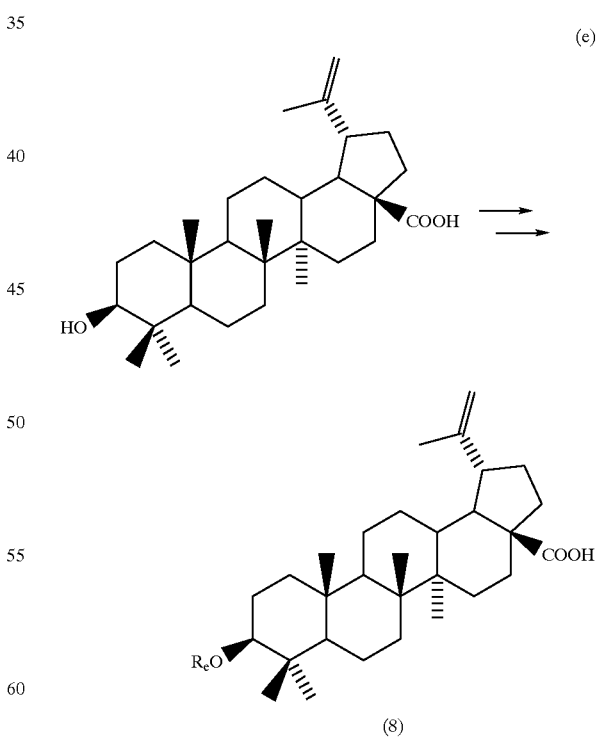

(8)

wherein $R_e$=$R_1CO$ or $XC_6H_4CO$.

With respect to modification at the C-28 position, the carboxyl group of betulinic acid can be converted to a number of esters (9) and amides (10) by reaction with an alcohol or an amine, respectively, as set forth in equations (f) and (g). Depending on the types of functional groups present on the alcohols or amines, additional structural modification are possible. The carboxyl group also can be converted to a salt, in particular an alkali metal salt, an alkaline earth salt, an ammonium salt, an alkylammonium salt, a hydroxyalkyl ammonium salt, or a transition metal salt.

philes to provide an amino (11) or an ether derivative (12), as set forth in equations (h) and (i).

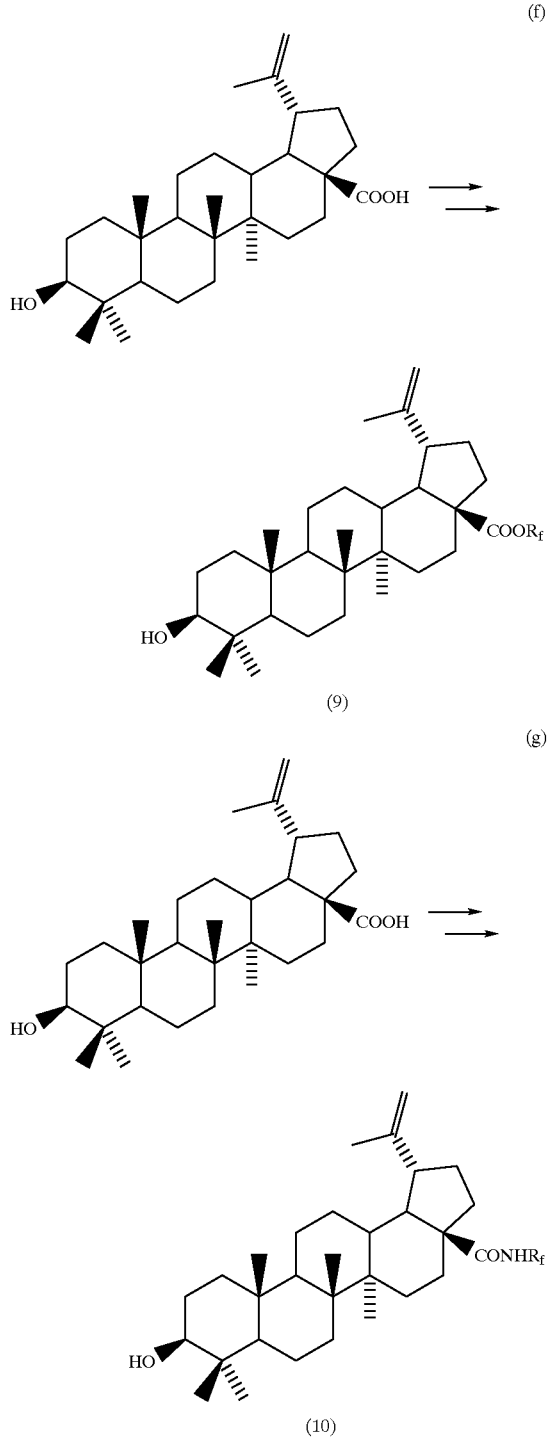

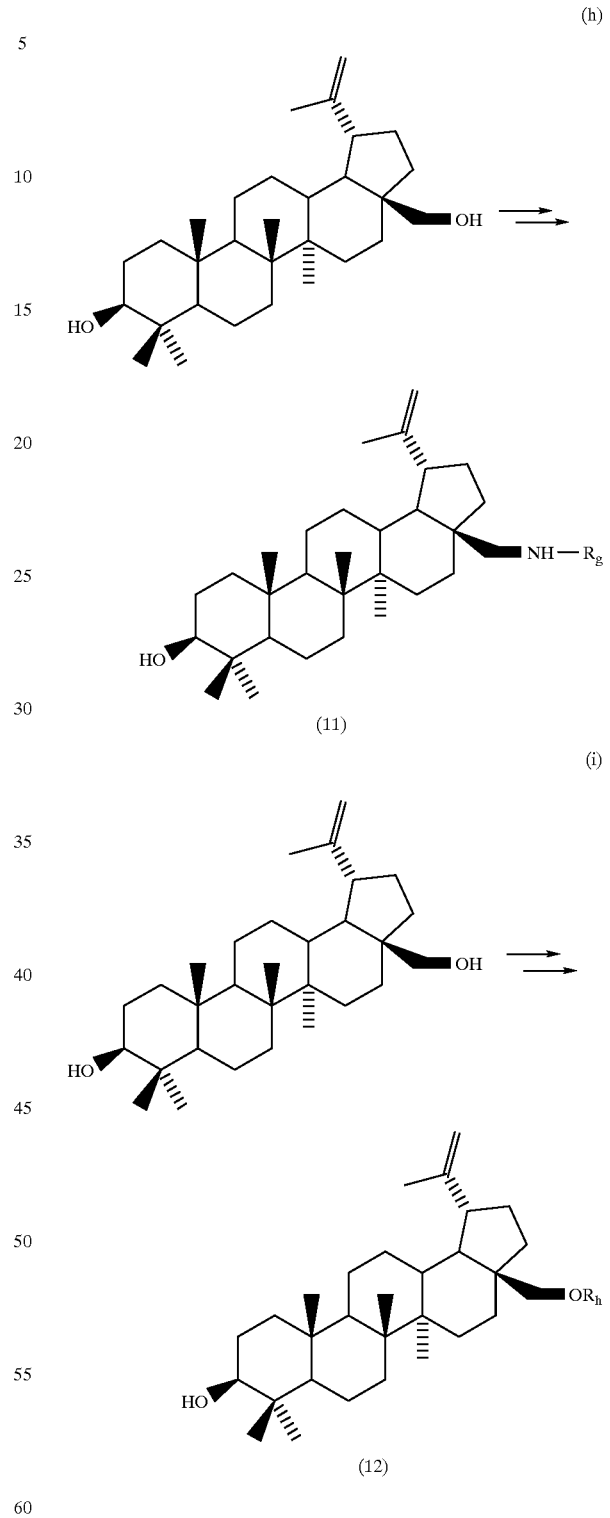

wherein $R_f$=$C_1$–$C_{10}$ alkyl, phenyl, substituted phenyl ($C_6H_4X$); or $CH_2CCR_1$.

The activated C-28 hydroxyl group of betulin can undergo substitution reactions, like SN-2 type reactions, with nucleowherein $R_g$=H or $C_1$–$C_{16}$ alkyl, or $R_g$=$C_6H_4X$, and wherein $R_h$=$C_1$–$C_{16}$ alkyl or $C_6H_4X$.

The hydroxyl group at the C-28 position can be oxidized to yield an aldehyde, which in turn can react with hydroxylamine to provide a hydroxyloxime compound. The hydroxyloxime can react with a variety of electrophiles to provide the oxime derivatives (13), as set forth in equation (j).

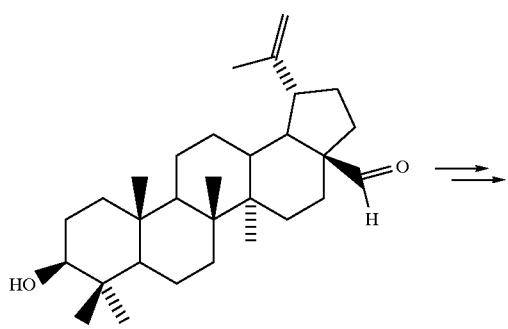

(j)

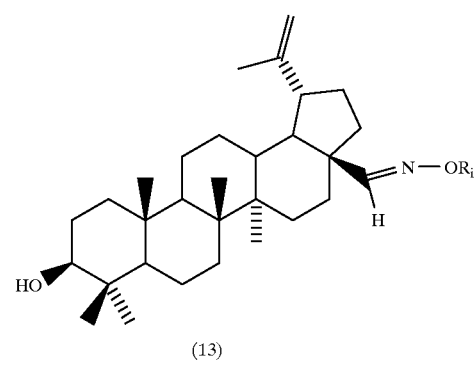

(13)

wherein $R_i$=H or $C_1$–$C_{16}$ alkyl, or $R_i$=COC$_6$H$_4$X, or $R_i$=COCH$_2$Y, or $R_i$=CH$_2$CHCH$_2$ or CH$_2$CCR$_1$.

The aldehyde at the C-28 position also can react with a series of lithium acetylide compounds to yield a variety of alkynyl betulin derivative (14), as set forth in equation (k).

(k)

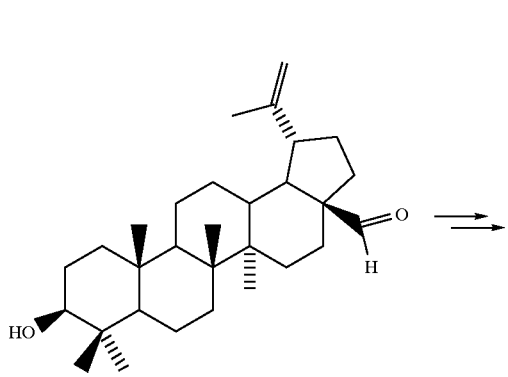

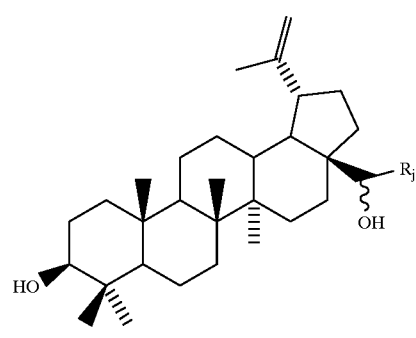

(14)

wherein $R_j$=CCR$_1$, wherein $R_1$=H or $C_1$–$C_6$ alkyl.

With respect to modifications at the C-20 position, the isoprenyl group at the C-20 position can be ozonized to yield a ketone (15) at C-20 position, as set forth in equation (l). A variety of reactions performed on the ketone functionality can provide a series of different derivatives. For example, the ketone functionality of compound (15) can be easily converted to a variety of oximes. Furthermore, a number of additional oxime derivatives (16) can be prepared through substitution reactions at the hydroxyl group of the hydroxyloxime with electrophiles, as set forth in equation (m).

(l)

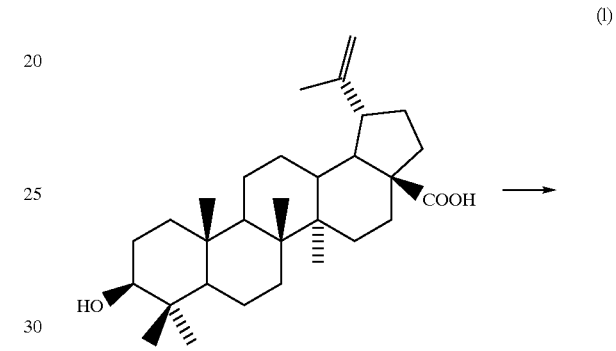

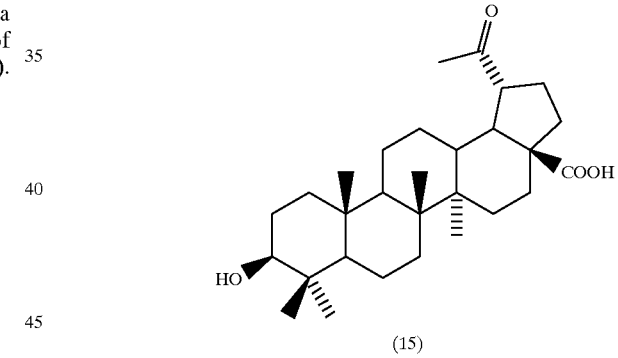

(15)

(m)

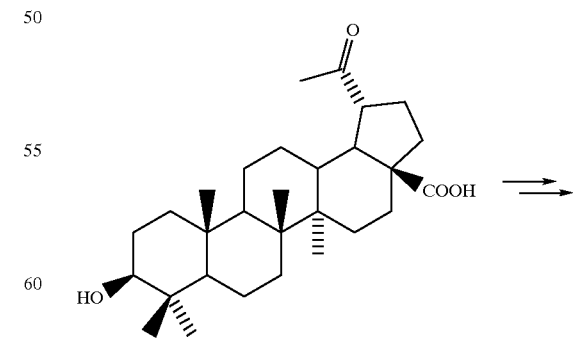

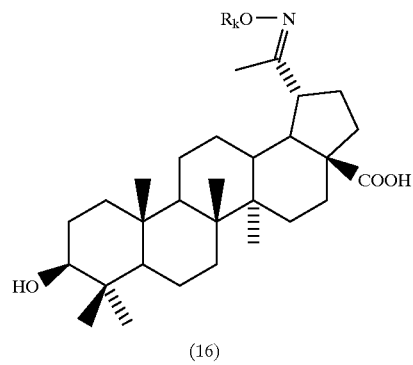

(16)

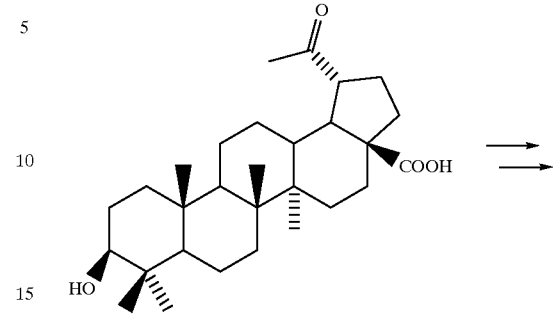

(18)

wherein $R_k$=H or $C_1$–$C_{16}$ alkyl, or $R_k$=COC$_6$H$_4$X or $R_k$=COCH$_2$Y, or $R_k$=CH$_2$CHCH$_2$ or CH$_2$CCR$_1$.

The ketone functionality also can undergo a reductive amination reaction with a series of aliphatic and aromatic amines in the presence of NaBH$_3$CN to provide a corresponding substituted amine (17) at the C-20 position, as set forth in equation (n).

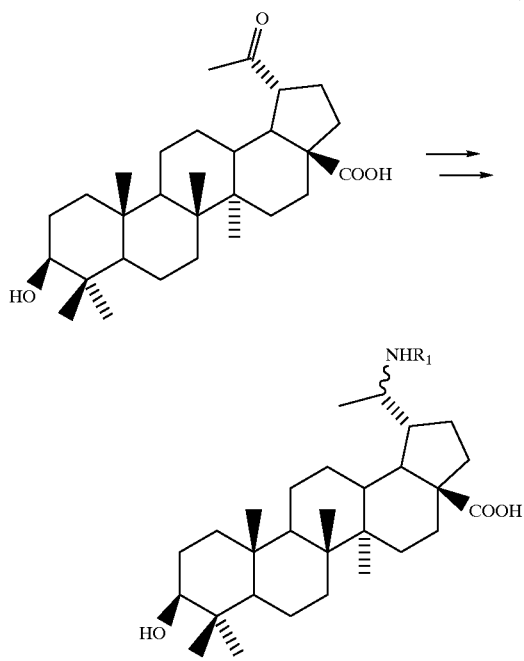

(17)

(n)

wherein $R_l$=C$_1$–C$_{16}$ alkyl, or $R_l$=C$_6$H$_4$X, or $R_l$=COC$_6$H$_4$X, or $R_l$=COCH$_2$Y, or $R_l$=CH$_2$CHCH$_2$ or CH$_2$CCR$_1$.

The ketone can be reacted with a series of lithium acetylides to provide alkynyl alcohol derivatives (18) at the C-20 position, as set forth in equation (o).

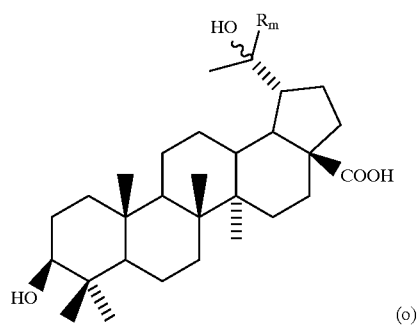

(o)

wherein, $R_m$=CCR$_1$.

The ketone further can be reduced to a secondary alcohol (19) to react with an acyl chloride to provide a series of esters (20) at the C-20 position, as set forth in equation (p).

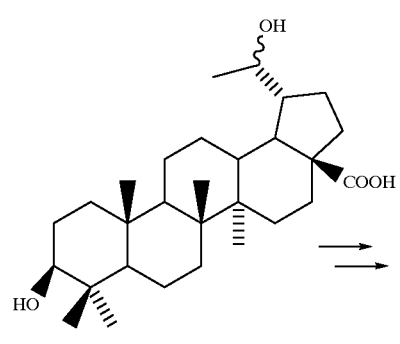

(19)

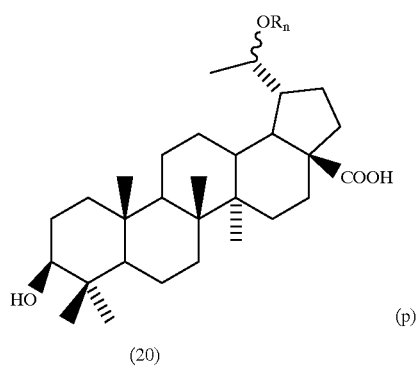

(20) (p)

wherein $R_n$=H, $C_1$–$C_{16}$ alkyl, $CH_2CCR_1$, or $R_n$=$CH_3CO$ or $XC_6H_4CO$.

In addition, a number of different derivatives can be prepared through a combinatorial chemical approach. For example, as set forth below, in the preparation of oximes at the C-20 position, a number of electrophiles, e.g., a variety of alkyl halides, can be added together in one reaction vessel containing the hydroxyloxime to provide a mixture of betulinic acid derivatives. Each reaction product in the mixture can be isolated by using semi-preparative HPLC processes using appropriate separation conditions, then submitted for bioassay.

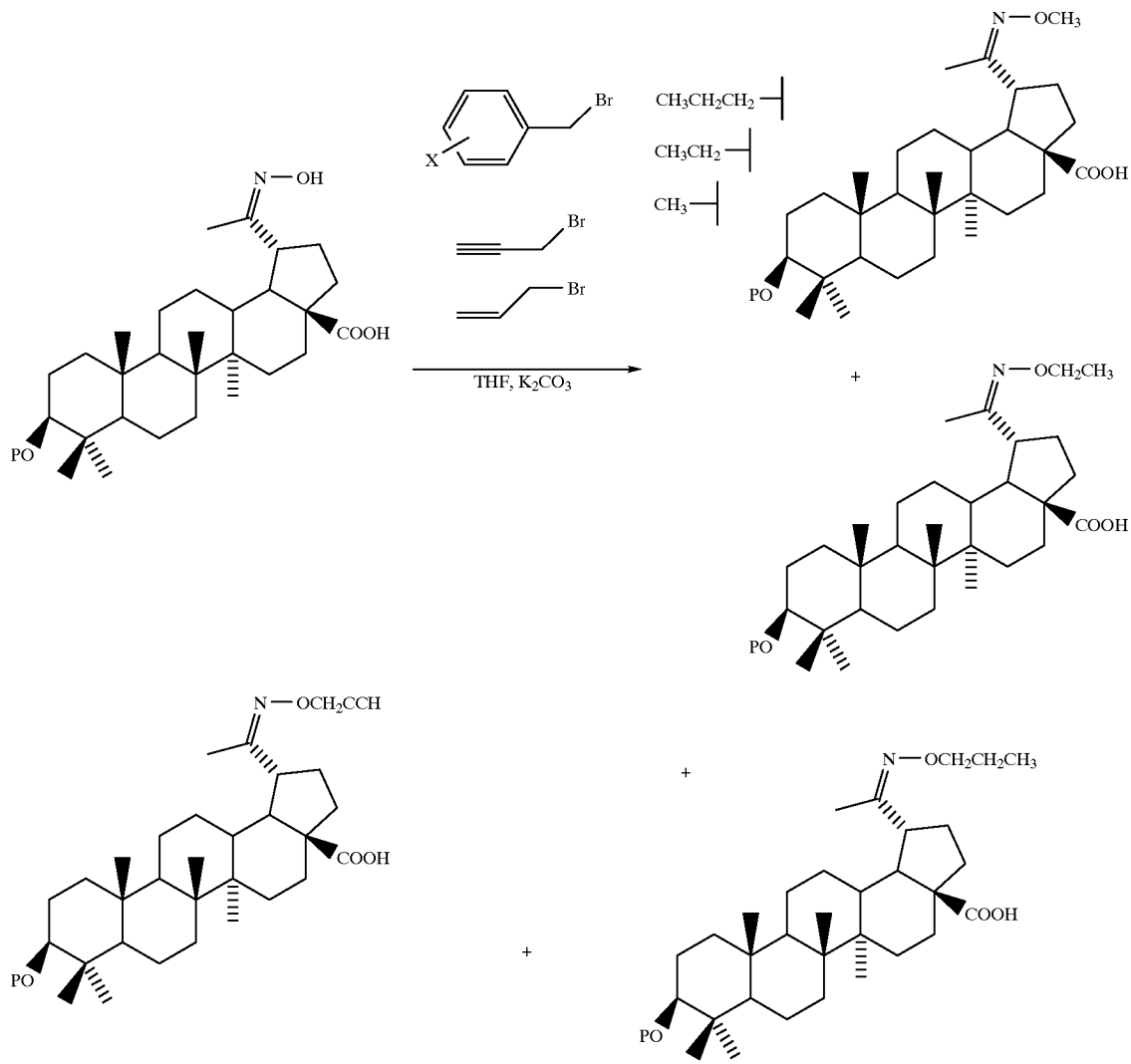

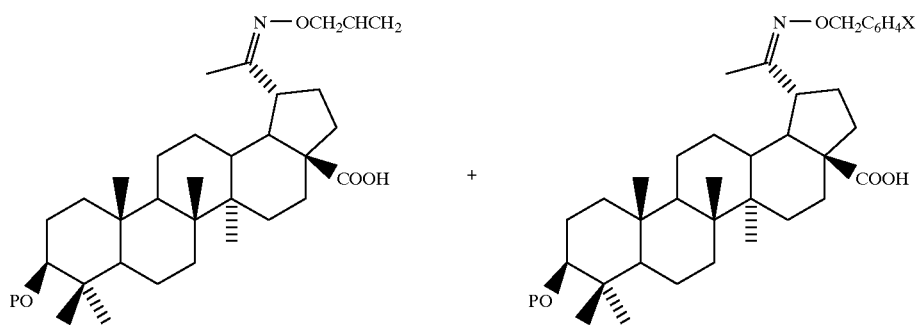

wherein P is a protecting group for the secondary alcohol functionality.

A low temperature reaction of betulonic acid with a mixture of lithium acetylides in a single reaction vessel, as set forth below, yielded a mixture of alkynyl alcohols at the C-3 position. Each component in the mixture can be isolated by using semipreparative HPLC processes using appropriate separation conditions, then submitted for bioassay.

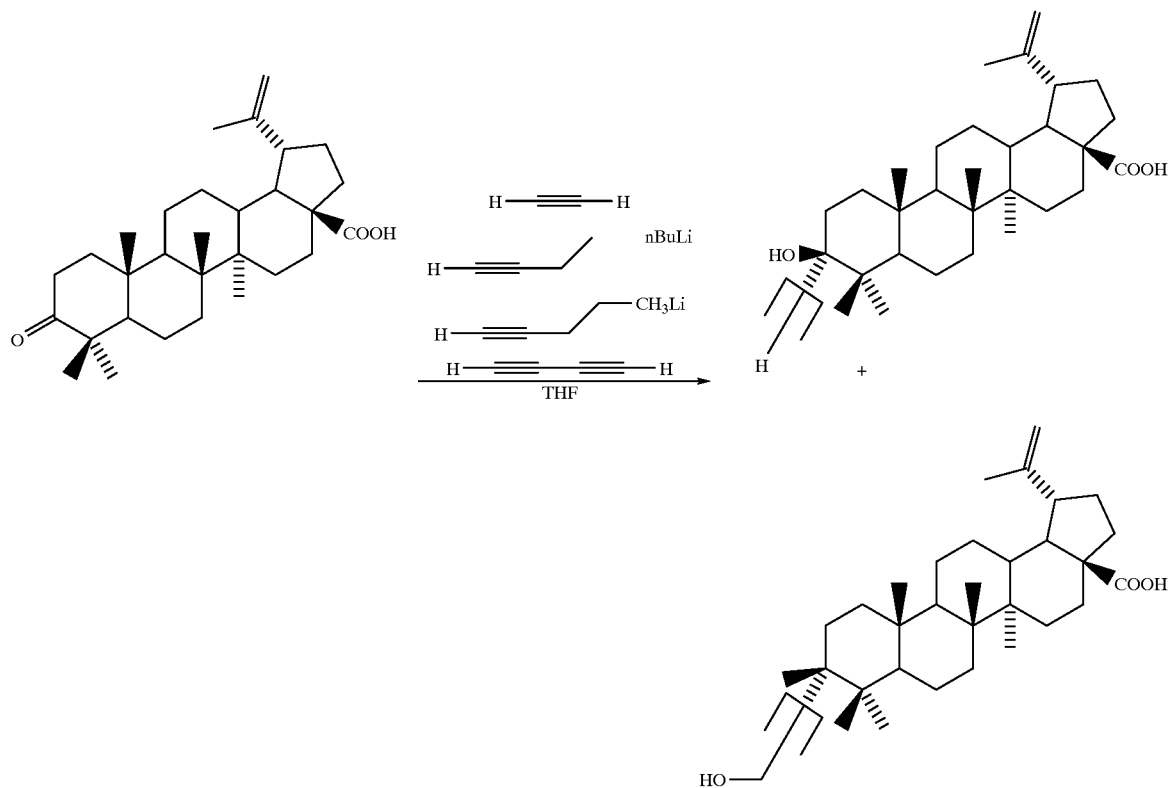

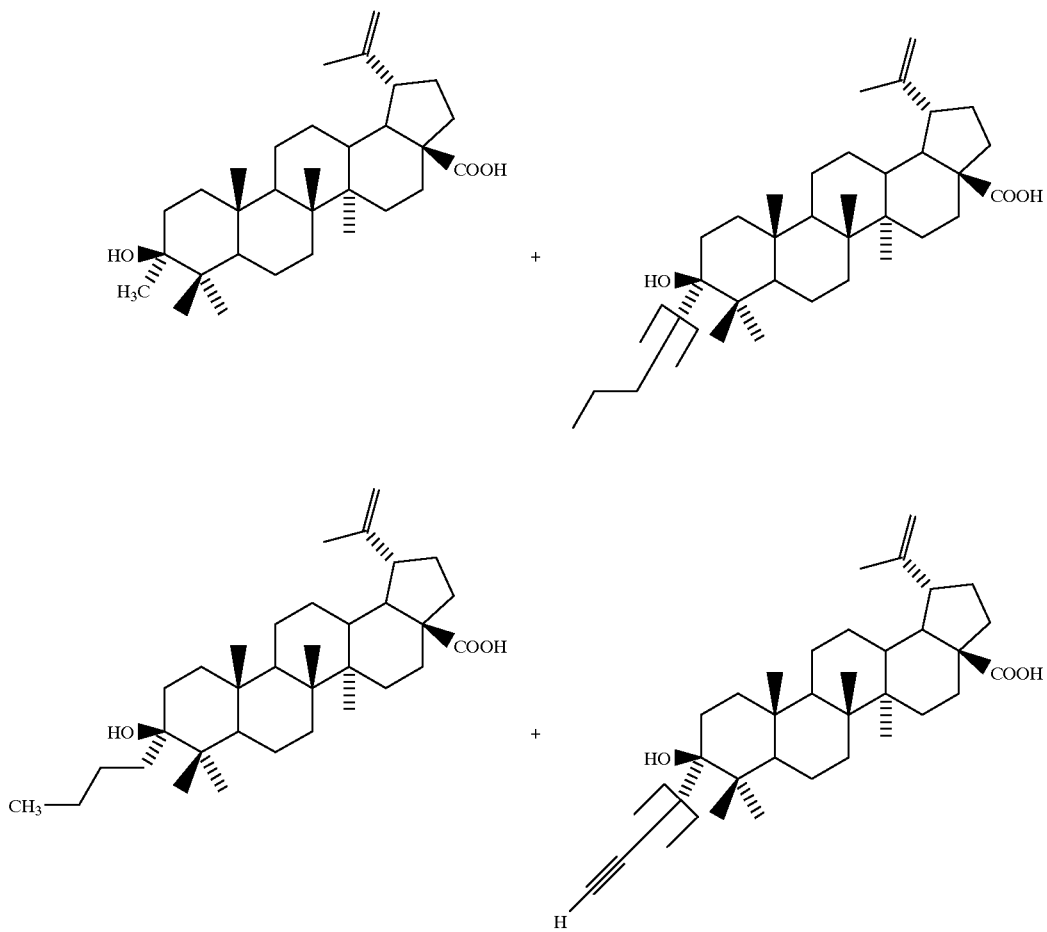

In order to demonstrate that betulinic acid derivatives have a potent bioefficacy, various derivatives were subjected to a series of biological evaluation tests. The biological evaluation of the derivatives focused on the activity against human melanoma cell lines. In particular, the following betulinic acid derivatives were prepared and tested for cytotoxicity profile against human melanoma cell lines and against a number of selected nonmelanoma cell lines. The results are summarized in Table 4. The data shows that some hydrogenated derivatives, i.e., compounds 5 and 11, are less active than nonhydrogenated derivatives 13 and 10, respectively. However, other hydrogenated derivatives, i.e., compounds 7 and 6, showed a comparable biological activity to nonhydrogenated derivatives 2 and 8, respectively. Therefore, it is possible to optimize the modification at the C-20 position to yield more potent betulinic acid derivatives. Table 4 contains a summary of data showing the effect of hydrogenation at the C-20 position.

TABLE 4

Cytotoxicity Data of Betulinic Acid Derivatives

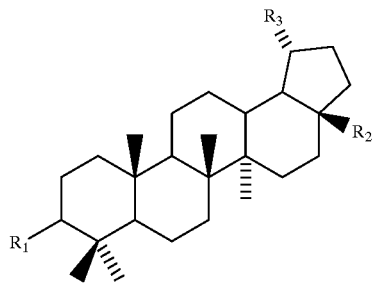

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 1 | O= | CHO | CH$_2$=C(CH$_3$)$_2$ | 7.4 (2.4) | >20 | 3.2 (1.2) | >20 | 18.5 | 12.9 |
| 2 | HO—N= | COOH | CH$_2$=C(CH$_3$)$_2$ | 2.4 (0.3) | 14.8 (2.0) | 1.9 (1.0) | 15.8 | 9.1 | >20 |
| 3 | CH$_3$O—N= | CHNOCH$_3$ | CH$_2$=C(CH$_3$)$_2$ | >20 | >20 | >20 | >20 | >20 | 20 |
| 4 | HO—N= | CHNOH | CH$_2$=C(CH$_3$)$_2$ | 2.2 (0.7) | 11.9 (2.7) | 1.4 (0.6) | 17.5 | 4.1 | 3.3 |
| 5 | CH$_3$O—N= | COOH | C(CH$_3$)$_3$ | >20 | >20 | >20 | >20 | | |
| 6 (Dihydrobetulonic acid) | O= | COOH | C(CH$_3$)$_3$ | 0.7 (0.6) | 10.8 (2.6) | 0.9 (0.4) | 20 | | |
| 7 | HO—N= | COOH | C(CH$_3$)$_3$ | 2.2 (0.3) | 13.1 (1.1) | 1.6 (1.1) | 13.9 | | |
| 8 (Betulonic acid) | O= | COOH | CH$_2$=C(CH$_3$)$_2$ | 0.9 (0.8) | 15.3 (3.4) | 0.4 (0.1) | 20 | 6.9 | 2.5 |
| 9 | H$_2$N— | COOH | CH$_2$=C(CH$_3$)$_2$ | 1.3 (0.4) | 52 (2.6) | 1.3 (0.5) | 3.1 | | |
| 10 (Betulinic acid) | HO— | COOH | CH$_2$=C(CH$_3$)$_2$ | 1.2 (0.1) | 6.2 (1.5) | 1.0 (0.3) | 17.6 (0.5) | >20 | >20 |
| 11 (Dihydrobetulinic acid) | HO— | COOH | C(CH$_3$)$_3$ | 5.8 | | | | >20 | >20 |
| 12 (Betulin) | HO— | CH$_2$OH | CH$_2$=C(CH$_3$)$_2$ | >20 | | | | >20 | >20 |
| 13 | CH$_3$O—N= | COOH | CH$_2$=C(CH$_3$)$_2$ | 8.3 | | | | >20 | 4.3 |
| 14 (Methyl betulinate) | HO— | COOCH$_3$ | CH$_2$=C(CH$_3$)$_2$ | 8.3 | | | | 12.5 | 11.8 |
| 15 (Lupeol) | HO— | CH$_3$ | CH$_2$=C(CH$_3$)$_2$ | 17.6 | | | | 15.6 | >20 |
| 16 (Lupeol benzoate) | C$_6$H$_4$COO— | CH$_3$ | CH$_2$=C(CH$_3$)$_2$ | >20 | | | | >20 | >20 |

MEL-2, MEL-6, MEL-8, MALE-3M, and LOX are melanoma cell lines, and KB is human oral epidermoid carcinoma.

TABLE 5

Cytotoxicity Data of Betulinic Acid Derivatives (Effect of Hydrogenation at C-20)

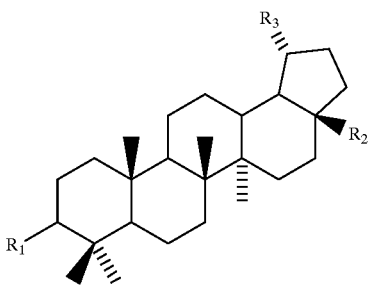

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 13 | CH$_3$O—N= | COOH | CH$_2$=C(CH$_3$)$_2$ | 8.3 | | | | >20 | 4.3 |
| 5 | CH$_3$O—N= | COOH | C(CH$_3$)$_3$ | >20 | >20 | >20 | >20 | | |
| 10 (Betulinic acid) | HO— | COOH | CH$_2$=C(CH$_3$)$_2$ | 1.2 (0.1) | 13.2 (1.5) | 1.0 (0.3) | 17.6 (0.5) | >20 | >20 |
| 11 | HO— | COOH | C(CH$_3$)$_3$ | 5.8 | | | | >20 | >20 |

TABLE 5-continued

Cytotoxicity Data of Betulinic Acid Derivatives (Effect of Hydrogenation at C-20)

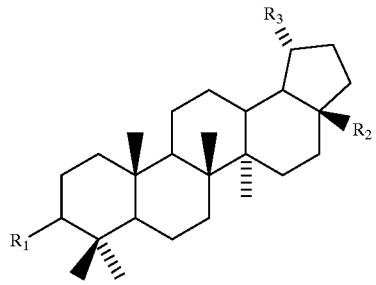

| Compound | $R_1$ | $R_2$ | $R_3$ | MEL-2 | MEL-6 | MEL-8 | MALE-3M | LOX | KB |
|---|---|---|---|---|---|---|---|---|---|
| | | | | \multicolumn{6}{c}{$ED_{50}$ [μg/mL] (Std. Dev.)} |
| (Dihydrobetulinic acid) 2 | HO—N= | COOH | $CH_2=C(CH_3)_2$ | 2.4 (0.3) | 14.8 (2.0) | 1.9 (1.0) | 15.8 | 9.1 | >20 |
| 7 | HO—N= | COOH | $C(CH_3)_3$ | 2.2 (0.3) | 13.1 (1.1) | 1.6 (1.1) | 13.9 | | |
| 8 (Betulonic acid) | O= | COOH | $CH_2=C(CH_3)_2$ | 0.9 (0.8) | 15.3 (3.4) | 0.4 (0.1) | 20 | 6.9 | 2.5 |
| 6 (Dihydrobetulonic acid) | O= | COOH | $C(CH_3)_3$ | 0.7 (0.6) | 10.8 (2.6) | 0.9 (0.4) | 20 | | |

The modification of betulinic acid at the C-3 position showed that all compounds, except methoxy oxime 13, expressed a comparable biological activity toward melanoma cell lines (Table 6). Amino compound 9 exhibited an improved cytotoxicity compared to betulinic acid 10. Compounds 2, 8, and 13 showed a decrease in selective cytotoxicity compared to betulinic acid.

TABLE 6

Cytotoxicity Data of Betulinic Acid Derivatives (Modification at C-3 Position)

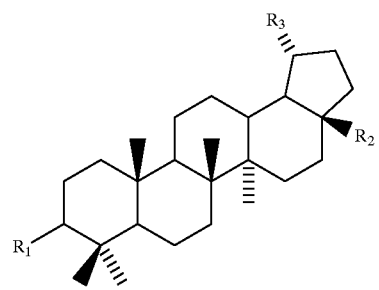

| Compound | $R_1$ | $R_2$ | $R_3$ | MEL-2 | MEL-6 | MEL-8 | MALE-3M | LOX | KB |
|---|---|---|---|---|---|---|---|---|---|
| | | | | \multicolumn{6}{c}{$ED_{50}$ [μg/mL] (Std. Dev.)} |
| 10 (Betulinic acid) | HO— | COOH | $CH_2=C(CH_3)_2$ | 1.2 (0.1) | 13.2 (1.5) | 1.0 (0.3) | 17.6 (0.5) | >20 | >20 |
| 8 (Betulonic acid) | O= | COOH | $CH_2=C(CH_3)_2$ | 0.9 (0.8) | 15.3 (3.4) | 0.4 (0.1) | 20 | 6.9 | 2.5 |
| 2 | HO—N= | COOH | $CH_2=C(CH_3)_2$ | 2.4 (0.3) | 14.8 (2.0) | 1.9 (1.0) | 15.8 | 9.1 | >20 |
| 13 | $CH_3O$—N= | COOH | $CH_2=C(CH_3)_2$ | 8.3 | | | | >20 | 4.3 |
| 9 | $H_2N$— | COOH | $CH_2=C(CH_3)_2$ | 1.3 (0.4) | 5.2 (2.6) | 1.3 (0.5) | 3.1 | | |

With respect to modifications at the C-28 position, the free carboxylic acid group at C-28 position is important with respect to expression of biological activity (Table 7). However, it is unknown whether the size or the strength of hydrogen bonding or the nucleophilicity of the C-28 substituents is responsible for the biological effect.

TABLE 7

Cytotoxicity Data of Betulinic Acid Derivatives (Modification at C-28 Position)

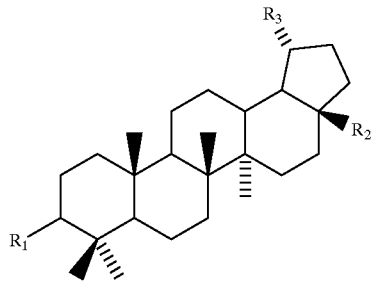

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 12 (Betulin) | HO— | CH$_2$OH | CH$_2$=C(CH$_3$)$_2$ | >20 | | | | >20 | >20 |
| 10 (Betulinic acid) | HO— | COOH | CH$_2$=C(CH$_3$)$_2$ | 1.2 (0.1) | 13.2 (1.5) | 1.0 (0.3) | 17.6 (0.5) | >20 | >20 |
| 14 (Methyl betulinate) | HO— | COOCH$_3$ | CH$_2$=C(CH$_3$)$_2$ | 8.3 | | | | 12.5 | 11.8 |
| 15 (Lupeol) | HO— | CH$_3$ | CH$_2$=C(CH$_3$)$_2$ | 17.6 | | | | 15.6 | >20 |

The biological activity changes attributed to oximes is illustrated in Table 8. The hydroxyloxime 4 improved the cytotoxicity profile, although selectivity was lost. It appears that the size of the substituent and its ability to hydrogen bond may influence the expression of the biological activity.

TABLE 8

Cytotoxicity Data of Betulinic Acid Derivatives (Effect by Oximes)

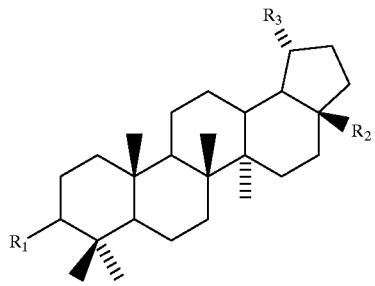

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 12 (Betulin) | HO— | CH$_2$OH | CH$_2$=C(CH$_3$)$_2$ | >20 | | | | >20 | >20 |
| 1 | O= | CHO | CH$_2$=C(CH$_3$)$_2$ | 7.4 (2.4) | >20 | 3.2 (1.2) | >20 | 18.5 | 12.9 |
| 4 | HO—N= | CHNOH | CH$_2$=C(CH$_3$)$_2$ | 2.2 (0.7) | 11.9 (2.7) | 1.4 (0.6) | 17.5 | 4.1 | 3.3 |
| 3 | CH$_3$O—N= | CHNOCH$_3$ | CH$_2$=C(CH$_3$)$_2$ | >20 | >20 | >20 | >20 | >20 | >20 |

The above tests show that modifying the parent structure of betulinic acid can provide derivatives which can be used as potent antitumor drugs against melanoma and other cancer cell lines. Betulinic acid derivatives having a comparable or better antitumor activity than betulinic acid against human melanoma have been prepared. In addition, even though betulinic acid has a remarkably selective antitumor activity, betulinic acid also has a poor solubility in water. The low solubility of betulinic acid in water can be overcome by introducing an appropriate substituent on the parent structure, which in turn can further improve selective antitumor activity. In addition, because the parent compound, betulinic acid, has shown to possess anti-HIV activity, the derivatives also can be developed as potential anti-HIV drug candidates.

What is claimed is:

1. A method of inhibiting growth of a tumor comprising administering, to an individual, a therapeutically effective amount of betulinic acid to a tumor, wherein the tumor growth is a squamous tumor, a breast cancer, a colon cancer, a sarcoma, a human oral epidermoid carcinoma, a prostate cancer, a lung cancer, a glioma, or a neuroblastoma.

2. The method of claim 1 wherein the tumor is a neuroblastoma.

3. The method of claim 1 wherein the betulinic acid is administered topically, intravenously, or intraperitoneally.

* * * * *